US008520978B2

(12) United States Patent
Jakobovits

(10) Patent No.: US 8,520,978 B2
(45) Date of Patent: Aug. 27, 2013

(54) METHODS, COMPUTER PROGRAM PRODUCTS, APPARATUSES, AND SYSTEMS FOR FACILITATING VIEWING AND MANIPULATION OF AN IMAGE ON A CLIENT DEVICE

(75) Inventor: Rex Jakobovits, Seattle, WA (US)

(73) Assignee: McKesson Technologies Inc., Alpharetta, GA (US)

(*) Notice: Subject to any disclaimer, the term of this patent is extended or adjusted under 35 U.S.C. 154(b) by 1159 days.

(21) Appl. No.: 12/262,668

(22) Filed: Oct. 31, 2008

(65) Prior Publication Data

US 2009/0274384 A1 Nov. 5, 2009

Related U.S. Application Data

(60) Provisional application No. 60/984,291, filed on Oct. 31, 2007.

(51) Int. Cl.
G06K 9/32 (2006.01)
G06K 9/54 (2006.01)
G06F 15/16 (2006.01)

(52) U.S. Cl.
USPC ............ 382/299; 382/305; 709/219

(58) Field of Classification Search
USPC .................................................... 382/299
See application file for complete search history.

(56) References Cited

U.S. PATENT DOCUMENTS

| 4,945,476 A | 7/1990 | Bodick et al. |
| 5,542,003 A | 7/1996 | Wofford |
| 5,583,758 A | 12/1996 | McIlroy et al. |
| 5,664,109 A | 9/1997 | Johnson et al. |
| 5,710,835 A * | 1/1998 | Bradley .................. 382/233 |
| 5,724,070 A * | 3/1998 | Denninghoff et al. ........ 345/547 |
| 5,835,735 A | 11/1998 | Mason et al. |
| 5,854,851 A | 12/1998 | Bamberger et al. |
| 5,953,704 A | 9/1999 | McIlroy et al. |
| 5,970,164 A | 10/1999 | Bamberger et al. |
| 6,101,407 A | 8/2000 | Groezinger |
| 6,167,442 A | 12/2000 | Sutherland et al. |

(Continued)

FOREIGN PATENT DOCUMENTS

WO WO 2006/118628 A2 11/2006

OTHER PUBLICATIONS

Koichi et al., Longitudinal Storage of Medical Images Using Transformation of DICOM to JPEG, Dialog/2004 Japan Science and Tech Corp (JST), abstract, partial, p. 1, available at http://sciencelinks.jp/j-east/article/200120/000020012001A0334475.php.*

(Continued)

Primary Examiner — David Zarka
(74) Attorney, Agent, or Firm — Alston & Bird LLP

(57) ABSTRACT

A method, apparatus, and computer program product are provided to accommodate decision support and reference case management for diagnostic imaging. An apparatus may include a processor configured to receive a request for an image from a client device. The processor may be further configured to retrieve a source image corresponding to the requested image from a memory. The processor may additionally be configured to process the source image to generate a second image having a greater resolution than the source image. The processor may also be configured to provide the second image to the client device to facilitate viewing and manipulation of the second image at the client device. Corresponding methods and computer program products are also provided.

22 Claims, 10 Drawing Sheets

(56) References Cited

U.S. PATENT DOCUMENTS

| | | |
|---|---|---|
| 6,182,029 B1 | 1/2001 | Friedman |
| 6,260,021 B1 | 7/2001 | Wong et al. |
| 6,269,193 B1 | 7/2001 | Young et al. |
| 6,269,379 B1 | 7/2001 | Hiyama et al. |
| 6,304,277 B1 * | 10/2001 | Hoekstra et al. ............ 345/600 |
| 6,349,330 B1 | 2/2002 | Bernadett et al. |
| 6,349,373 B2 | 2/2002 | Sitka et al. |
| 6,424,996 B1 | 7/2002 | Killcommons et al. |
| 6,493,702 B1 | 12/2002 | Adar et al. |
| 6,564,256 B1 | 5/2003 | Tanaka |
| 6,574,629 B1 | 6/2003 | Cooke, Jr. et al. |
| 6,633,674 B1 | 10/2003 | Barnes et al. |
| 6,678,703 B2 | 1/2004 | Rothschild et al. |
| 6,792,151 B1 | 9/2004 | Barnes et al. |
| 6,795,583 B1 | 9/2004 | Barnes et al. |
| 6,912,317 B1 | 6/2005 | Barnes et al. |
| 6,934,698 B2 | 8/2005 | Judd et al. |
| 6,968,077 B1 | 11/2005 | Yamanaka |
| 6,987,945 B2 | 1/2006 | Corn et al. |
| 6,988,240 B2 | 1/2006 | Gröber et al. |
| 7,039,723 B2 | 5/2006 | Hu et al. |
| 7,047,235 B2 | 5/2006 | Yang et al. |
| 7,080,098 B2 | 7/2006 | Smirniotopoulos et al. |
| 7,106,479 B2 | 9/2006 | Roy et al. |
| 7,106,890 B1 | 9/2006 | Grant et al. |
| 7,127,445 B2 | 10/2006 | Mogi et al. |
| 7,171,625 B1 | 1/2007 | Sacchi |
| 7,181,617 B2 | 2/2007 | Wise et al. |
| 7,194,474 B2 | 3/2007 | Birdwell et al. |
| 7,280,702 B2 * | 10/2007 | Chang et al. .................. 382/240 |
| 7,440,626 B2 | 10/2008 | Kong et al. |
| 7,457,656 B2 | 11/2008 | Judd et al. |
| 8,055,636 B2 | 11/2011 | Judd et al. |
| 2001/0019587 A1 | 9/2001 | Hashimoto et al. |
| 2002/0059288 A1 | 5/2002 | Yagi et al. |
| 2002/0167552 A1 | 11/2002 | Senda |
| 2003/0061071 A1 | 3/2003 | Babula et al. |
| 2004/0005094 A1 * | 1/2004 | Huffman ...................... 382/232 |
| 2004/0107118 A1 | 6/2004 | Harnsberger et al. |
| 2004/0141661 A1 | 7/2004 | Hanna et al. |
| 2004/0143645 A1 | 7/2004 | Cheenath |
| 2004/0249806 A1 | 12/2004 | Kanada |
| 2005/0005241 A1 | 1/2005 | Hunleth et al. |
| 2005/0021780 A1 | 1/2005 | Beyda |
| 2005/0043966 A1 | 2/2005 | Harnsberger et al. |
| 2005/0108052 A1 | 5/2005 | Omaboe |
| 2005/0108058 A1 | 5/2005 | Weidner et al. |
| 2005/0108365 A1 * | 5/2005 | Becker et al. ................. 709/219 |
| 2005/0129319 A1 | 6/2005 | Lee et al. |
| 2005/0237324 A1 | 10/2005 | Guhring |
| 2005/0251012 A1 | 11/2005 | Judd et al. |
| 2005/0271283 A1 | 12/2005 | Dekel et al. |
| 2006/0020622 A1 | 1/2006 | Shelton |
| 2006/0025670 A1 | 2/2006 | Kim et al. |
| 2006/0025671 A1 | 2/2006 | Kusunoki |
| 2006/0082809 A1 | 4/2006 | Loukipoudis et al. |
| 2006/0112142 A1 * | 5/2006 | Sako et al. .................. 707/104.1 |
| 2006/0168338 A1 | 7/2006 | Bruegl et al. |
| 2006/0170693 A1 | 8/2006 | Bethune et al. |
| 2006/0210196 A1 | 9/2006 | Wensley et al. |
| 2006/0229911 A1 | 10/2006 | Gropper et al. |
| 2006/0242148 A1 | 10/2006 | Rothpearl et al. |
| 2006/0274928 A1 | 12/2006 | Collins et al. |
| 2007/0035551 A1 | 2/2007 | Ubillos |
| 2007/0067184 A1 | 3/2007 | Harp et al. |
| 2007/0067252 A1 | 3/2007 | Hengerer et al. |
| 2007/0118540 A1 | 5/2007 | Guo |
| 2007/0118550 A1 | 5/2007 | Yang et al. |
| 2007/0208994 A1 | 9/2007 | Reddel et al. |
| 2008/0025583 A1 | 1/2008 | Jabri et al. |
| 2008/0084415 A1 | 4/2008 | Gundel |
| 2010/0063992 A1 | 3/2010 | Ma et al. |
| 2011/0110568 A1 | 5/2011 | Vesper et al. |

OTHER PUBLICATIONS

Jayalath, R. et al., "Quantification of Abdominal Aortic Calcification on CT", American Heart Association, Feb. 2006, pp. 429-430.
Sachs, J., "Image Resampling", Digital Light & Color, 2001.
Transmittal of International Preliminary Report on Patentability for International Application No. PCT/US2007/085292 mailed Jun. 4, 2009.
Notification of Transmittal of the International Search Report and the Written Opinion for International Application No. PCT/US07/85292 mailed May 20, 2008.
Non-Final Office Action for U.S. Appl. No. 11/943,388 dated Jan. 29, 2010.
Office Action for U.S. Appl. No. 11/943,355 dated Apr. 26, 2011.
Office Action for U.S. Appl. No. 12/262,714 dated Oct. 6, 2011.
Office Action for U.S. Appl. No. 12/262,714 dated Feb. 14, 2011.
Office Action mailed Sep. 30, 2010, for U.S. Appl. No. 11/943,355.
Garrett, J. J., *Ajax: A New Approach to Web Applications*, Published by Adaptive Path, Feb. 18, 2005, 5 pages.
Supplementary European Search Report for Appl. No. EP 07 86 4684 mailed Mar. 11, 2010.
Office Action in U.S. Appl. No. 11/943,388 dated Aug. 19, 2010.
Office Action for U.S. Appl. No. 11/943,388, mailed May 16, 2012.
Office Action for U.S. Appl. No. 12/201,417, mailed May 24, 2012.
Balani, N., et. al, "Build apps using Asynchronous JavaScript with XML (AJAX)", Nov. 15, 2005, IBM.
Green, B.C.; , "Web Access to DICOM Objects ("WADO")", May 1, 2009, UtraRAD Corporation.
Murray, G.; "Asynchronous JavaScript Technology and XML (AJAX) With the Java Platform", Oct. 2006, Oracle.
Powell, M.; "Asynchronous Web Service Calls over HTTP with the .NET Framework", Sep. 9, 2002, Microsoft.
Office Action for U.S. Appl. No. 12/201,417, mailed Dec. 16, 2011.
Office Action for U.S. Appl. No. 11/943,355, mailed Feb. 27, 2012.
Digital Imaging & Communications in Medicine (DICOM), Part 9, Communication Support for Message Exchange (National Electrical Manufacturers Association, Copyright 2007); 68 pages.
Kaldoudi, et al.; "*A Service Based Approach for Medical Image Distribution in Healthcare Intranets;*" Computer Methods and Programs in Biomedicine, vol. 18; dated 2006; retrieved on Feb. 14, 2013 from <http://www.researchgate.net/go.To.html?u=http%3A%2F%2Firis.med.duth.gr%2FPortals%2F14%2Fpub03_journal_papers%2FKaldoudi_2006_WS.pdf&ev=pub_ext_doc_dlext>.
Koutelakis, et al.; "*PACS through Web Compatible with DICOM Standard and WADO Service Advantages and Implementation;*" EMBS Annual International Conference; IEEE; dated Sep. 3, 2006; retrieved on Feb. 14, 2013 from <http://www.google.com/url?sa=t&rct=j&q=pacs%20through%20web%20compatible%20with%20dicom%20standard%20and%20wado%20service%20advantages%20and%20implementation&source=web&cd=2&ved=0CE8QFjAB&url=https%3A%2F%2Fwww2.lirmm.fr%2Flirmm%2Finterne%2F BIBLI%2FCDROM%2FROB%2F2006%2FEMBC_2006%2FPDFs%2FPapers%2F0196.pd f&ei=cVkdUaqBEMae2-wXU0YB4&usg=AFQjCNEhY9Jt2PgqbLXuS9O4d1Er5HhJ1Q&bvm=bv.42452523,d.b2I>.
Office Action for U.S. Appl. No. 11/943,388; dated Feb. 8, 2013.
Office Action from U.S. Appl. No. 12/262,714, mailed Jul. 30, 2012.

* cited by examiner

« BACK TO INBOX [Archive] [Report Spam] [Delete] [More actions... ▼]

MyPACS NEW CASE ALERT          Inbox
☆ Rex Jakobovits                       More options  8:07 pm (0 minutes ago)
THERE ARE 3 NEW CASES MATCHING YOUR ALERT CRITERIA:
[ Anatomy  =  "Heart",    Pathology  =  "Neoplasm" ]

📖 64 YEAR OLD M WITH 2 WEEK HISTORY OF FATIGUE ✉
Case 317700, 64 year old male, 3 images (CT, Conventional Radiograph)-
History: 64-year-old male who presented to the ED complaini...Diagnosis: Thymoma with
pure red cell aplasia. Keywds: thymoma.
By <u>Virginia Mason Medical Center</u>, Virginia Mason Medical Center, Washington, USA.

◇ ATRIAL MYXOMA ✉
Case 257601, 49 year old female, 1 CT Image.
History: Rule out PE. Diagnosis: Left Atrial Myxoma.
By <u>Mohammad Alsharabati</u>, Medical Student, University Of Jordan, Amman, Jordan.

◇ CARDIAC FIBROMA ✉
Case 94266, 18 year old patient, 7 images (CT, MR)
History: 18 yo with atypical chest pain with exertion. Diagnosis: Cardiac Fibroma.
By <u>Echo train</u>, Resident, Ohio State University Medical Center, Ohio, USA.

*FIG. 10*

[DELETE SELECTED SERIES]
☐–☑📁 All DICOM Queues
　　☑📁 DICOM Queue (7 series)
　　　☐☐ ANONYMIZED- (2006-10-23 13:33)
　　　☑📁 ANDERSON, Denise A.- 652044 - (2006-05-12 15:53) [used]
　　　　☑📁 CT-04-01765 - 2004-02-26 - ABD/PEL (sent 2006-05-12) [used]
　　　　　☑☐ S2 (66 CT)- (sent 15:53) [used]
　　　☐☐ CROSS, Louis - GE1242 - (2006-05-11 17:38) [used]
　　　☐☐ COTTA, Anna - SMS530102 - (2006-05-11 17:27) [used]
　　　☐☐ JANE, Doe - 123456 - (2006-05-11 17:16)
　　　☐☐ BAUM, Peter - SMS730815 - (2006-05-11 17:02)
　☐☐ Tumor Board Queue (0 series)
　☐☐ Nuclear Medicine Queue (0 series)

*FIG. 11*

SEARCH RESULTS                          Sort By: [relevance ▼]
Found 4 matching cases:
◇ EMBRYONAL CELL CARCINOMA TESTICLE WITH METASTATIC DISEASE
Case 10434, Genitourinary (GU) > Neoplasm, 16-year-old female, 8 images (CT, Conventional Radiograph, US)
History: 16-year-old male with history 16 y.o. male had CX...Diagnosis: Embryonal cell carcinoma
testicle with me...Keywds: embryonal cell carcinoma testicle metasta...
By <u>Rex Jakobovits</u>, 06/10/2005.

📖 OSTEOSARCOMA OF THE KNEE ✓                    ✉
Case 9943, Skeletal System > Neoplasm, 10-year-old female, 2 Conventional Radiograph images.
History: A 10 year old female c/o pain and swelling. Diagnosis: Osteosarcoma. Keywds: malignant
bone tumor.
By <u>Rex Jakobovits</u>, 06/10/2005.

📖 CARCINOMA OF THE RIGHT BREAST.       🔒
Case 10413, Breast > Neoplasm, 46-year-old female, 2 Conventional Radiograph images.
History: 46 y/o woman with sternal pain.
By <u>Rex Jakobovits</u>, 06/10/2005.

METHODS, COMPUTER PROGRAM PRODUCTS, APPARATUSES, AND SYSTEMS FOR FACILITATING VIEWING AND MANIPULATION OF AN IMAGE ON A CLIENT DEVICE

CROSS-REFERENCE TO RELATED APPLICATIONS

This application claims priority from U.S. Provisional Application No. 60/984,291, filed Oct. 31, 2007, entitled METHODS AND SYSTEMS TO ACCOMMODATE DECISION SUPPORT AND REFERENCE CASE MANAGEMENT FOR DIAGNOSTIC IMAGING, the contents of which are incorporated herein by reference.

FIELD OF THE INVENTION

Embodiments of the invention relate generally to tools, methods, computer program products, apparatuses, and systems for managing medical images and associated text and data, and more specifically, to the creation and use of medical image knowledge bases for decision support, reference, training, consultation, and collaboration.

BACKGROUND

Clinicians who interpret images make fewer errors when they are able to consult reference images and reference texts. When encountering challenging cases, clinicians frequently turn to textbooks or hunt for reference material on the web. However, the pressure of heavy workloads makes it infeasible for clinicians to consult reference material as often as they would like, as it takes a significant amount of searching to find good examples. Ideally, reference material takes the form of full diagnostic quality exams of known diagnoses, with key images identified and annotated. However, cases in textbooks and online often have only a few static images, usually too low resolution to be considered ideal for diagnosis. Hospital imaging systems and picture archiving and communication systems (PACS) often contain the images that the clinician needs for decision support, but the limited nature of existing retrieval interfaces makes it hard for clinicians to find the right studies.

Accordingly, it may be advantageous to provide methods, apparatuses, computer program products, and systems to accommodate decision support and reference case management for diagnostic imaging.

BRIEF SUMMARY OF THE INVENTION

Methods, apparatuses, computer program products, and systems are therefore provided, which may accommodate decision support and reference case management for diagnostic imaging. In this regard, some embodiments of the invention may provide several advantages to a user of a computing device seeking to view and manipulate medical data, such as medical images and medical case files. Embodiments of the invention may provide users with medical images of an enhanced resolution such that users may zoom in on and otherwise manipulate images while limiting problems with pixelization and distortion of images. Some embodiments of the invention may provide users with the ability to generate medical case files from an electronic message.

In one exemplary embodiment, a method is provided, which may include receiving a request for an image from a client device. The method may further include retrieving a source image corresponding to the requested image from a memory. The method may also include processing the source image to generate a second image having a greater resolution than the source image. The method may additionally include providing the second image to the client device to facilitate viewing and manipulation of the second image at the client device.

In another exemplary embodiment, a method is provided, which may include receiving an electronic message including a medical image from a picture archiving and communication system client. The method may further include parsing a subject line and body of the electronic message to extract text data included in the electronic message. The method may also include parsing a header associated with the medical image to determine one or more properties of the medical image. The method may additionally include generating a medical case file comprising the medical image. The method may further include populating one or more fields of the medical case file with the extracted text data and the determined properties.

In another exemplary embodiment, a computer program product is provided. The computer program product includes at least one computer-readable storage medium having computer-readable program instructions stored therein. The computer-readable program instructions may include a plurality of program instructions. Although in this summary, the program instructions are ordered, it will be appreciated that this summary is provided merely for purposes of example and the ordering is merely to facilitate summarizing the computer program product. The example ordering in no way limits the implementation of the associated computer program instructions. The first program instruction is for receiving a request for an image from a client device. The second program instruction is for retrieving a source image corresponding to the requested image from a memory. The third program instruction is for processing the source image to generate a second image having a greater resolution than the source image. The fourth program instruction is for providing the second image to the client device to facilitate viewing and manipulation of the second image at the client device.

In another exemplary embodiment, a computer program product is provided. The computer program product includes at least one computer-readable storage medium having computer-readable program instructions stored therein. The computer-readable program instructions may include a plurality of program instructions. Although in this summary, the program instructions are ordered, it will be appreciated that this summary is provided merely for purposes of example and the ordering is merely to facilitate summarizing the computer program product. The example ordering in no way limits the implementation of the associated computer program instructions. The first program instruction is for receiving an electronic message including a medical image from a picture archiving and communication system client. The second program instruction is for parsing a subject line and body of the electronic message to extract text data included in the electronic message. The third program instruction is for parsing a header associated with the medical image to determine one or more properties of the medical image. The fourth program instruction is for generating a medical case file comprising the medical image. The fifth program instruction is for populating one or more fields of the medical case file with the extracted text data and the determined properties.

In another exemplary embodiment, an apparatus is provided, which may include a processor. The processor may be configured to receive a request for an image from a client device. The processor may be further configured to retrieve a source image corresponding to the requested image from a memory. The processor may also be configured to process the source image to generate a second image having a greater resolution than the source image. The processor may additionally be configured to provide the second image to the client device to facilitate viewing and manipulation of the second image at the client device.

In another exemplary embodiment, an apparatus is provided, which may include a processor configured to receive an electronic message including a medical image from a picture archiving and communication system client. The processor may be further configured to parse a subject line and body of the electronic message to extract text data included in the electronic message. The processor may also be configured to parse a header associated with the medical image to determine one or more properties of the medical image. The processor may additionally be configured to generate a medical case file comprising the medical image. The processor may further be configured to populate one or more fields of the medical case file with the extracted text data and the determined properties.

Accordingly, embodiments of the invention make it easier for clinicians to consult and augment searchable repositories of reference cases for training and just-in-time reference for decision-support at the point of care. In various embodiments, the consultation and augmentation may be interactive and/or web-based. Embodiments of the invention may allow clinicians to add to the repository as part of their daily practice without disrupting their workflow, including techniques to efficiently tag or annotate medical images, series, exams, and subjects with diagnostic information, text, graphical annotations, and keywords, either directly from their existing medical imaging software (PACS, etc), or via a separate interface. Some embodiments of the system may automatically integrate the resulting local content with additional relevant reference content, including differentials, descriptions of findings, cases from third party institutions, and additional illustrative images. Embodiments of the invention may provide an interface for rapidly scanning through large collections of candidate images from multiple patients, and comparing these images side-by-side to a subject being diagnosed. Embodiments of the invention may give clinicians control over editing, sharing, retrieving, and interacting with the content from any browser. Fine-grained access control and versioning allows the content to be collaboratively evolved in a controlled fashion. The resulting system may provide convenient access to diagnostic-quality reference cases, both local and from third parties, organized by pathology and enhanced with discussions of findings and differentials.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

FIG. 10 illustrates an email alert according to an exemplary embodiment of the present invention;

FIG. 11 illustrates a DICOM queue manager according to an exemplary embodiment of the present invention;

FIG. 12 illustrates case abstracts according to an exemplary embodiment of the present invention;

Figure 13:
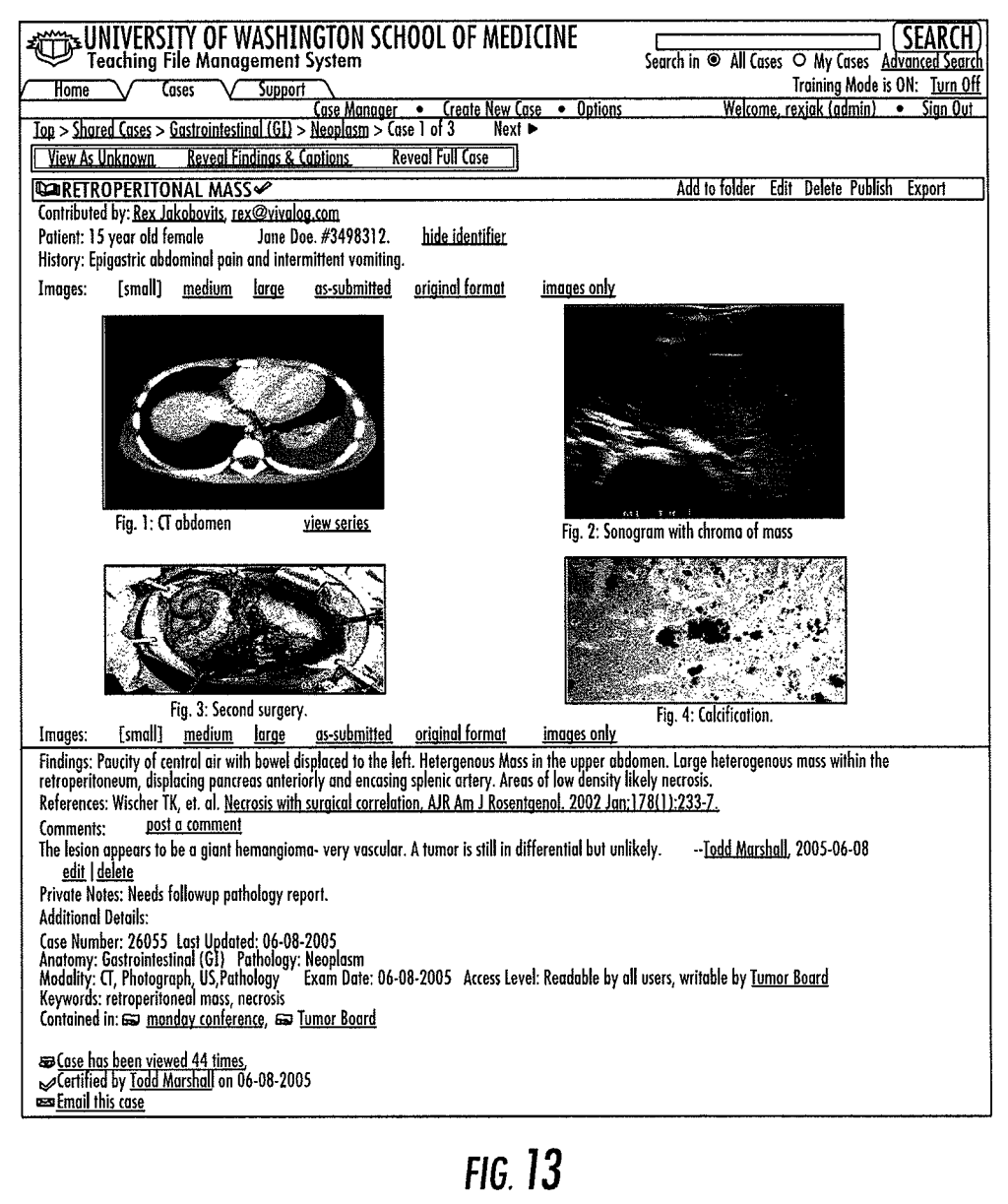

FIG. 13 illustrates a medical case viewer that is not embodied in JavaScript according to an exemplary embodiment of the present invention;

DETAILED DESCRIPTION OF THE INVENTION

Figure 1:
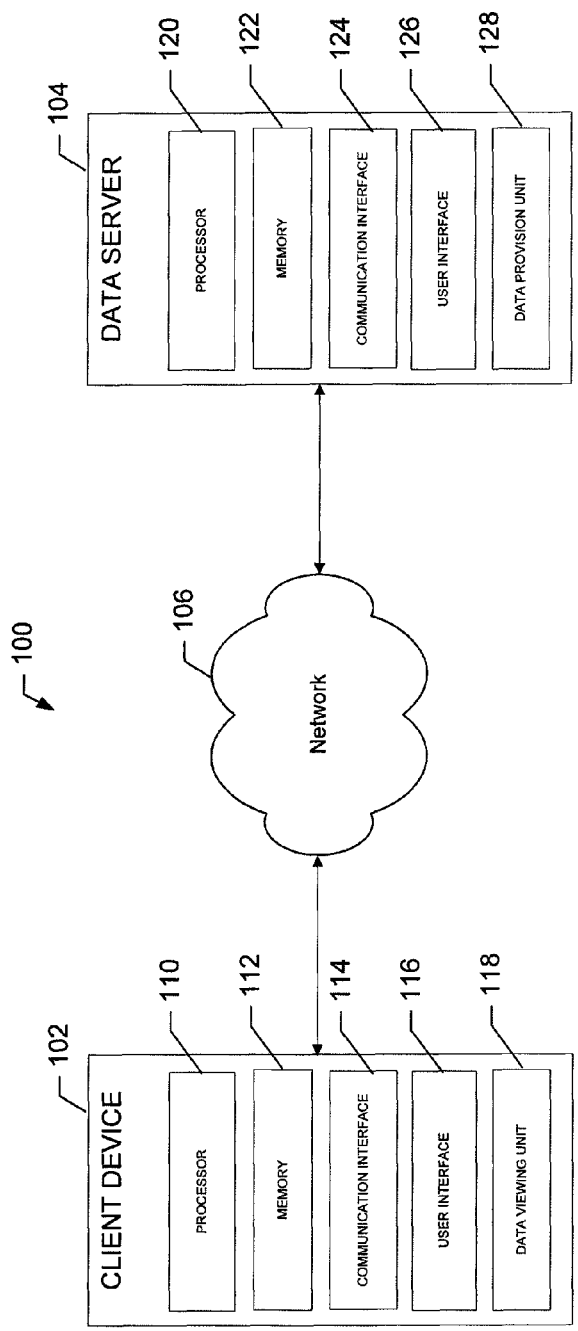
FIG. 1 illustrates a block diagram of a system for transmitting, viewing, and manipulating medical data according to an exemplary embodiment of the present invention.

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

Figure 2:
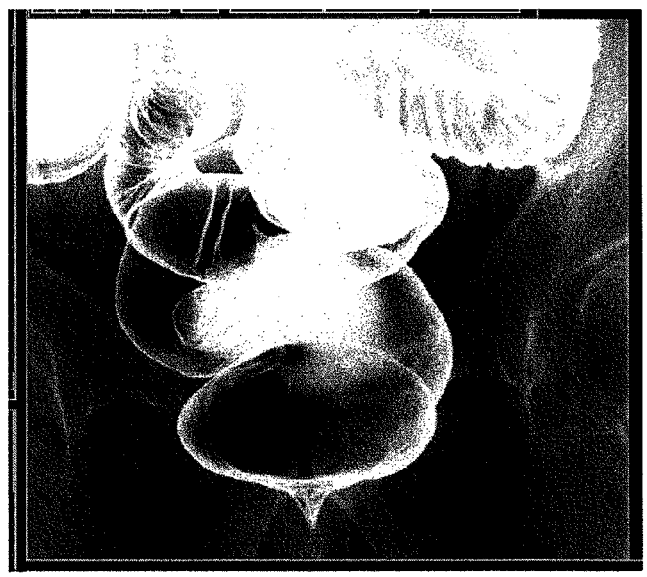
FIG. 2 illustrates a screenshot of a medical image, such as may be accessed, viewed and manipulated using embodiments of the present invention.

FIG. 1 illustrates a block diagram of a system 100 for viewing and manipulating medical data, such as, for example, medical images, diagnostic data, medical training data, other medical data, and/or the like according to an exemplary embodiment of the present invention. An example of a medical image that may be viewed and manipulated by the system 100 is illustrated in FIG. 2. As used herein, "exemplary" merely means an example and as such represents one example embodiment for the invention and should not be construed to narrow the scope or spirit of the invention in any way. It will be appreciated that the scope of the invention encompasses many potential embodiments in addition to those illustrated and described herein. As such, while FIG. 1 illustrates one example of a configuration of a system for viewing and manipulating medical data, numerous other configurations may also be used to implement embodiments of the present invention.

As used herein, "general purpose viewing agent" refers to any means, such as may be embodied in software, hardware, firmware, or some combination thereof that may be used to access, view, and interact with content. Such content may be located remotely from the computing device on which the general purpose viewing agent is embodied and may be accessed by the general purpose viewing agent over a network, such as the internet. In an exemplary embodiment, a general purpose viewing agent may be a web browser. Further, a general purpose viewing agent as used herein may implement one or more general graphics/animation services, which are generically described to be included as part of a "general purpose viewing agent" as used herein. A "general graphics/animation service" refers to any markup or scripting language that may be implemented by a general purpose viewing agent as well as any plug-in that may be installed in a general purpose viewing agent that is generally configured for a wide range of content viewing purposes and not specifically configured for a limited purpose or application. Such general graphics/animation services may include, for example, Adobe® Flash®, Adobe® Flex®, and Microsoft® Silverlight™, as well as markup and scripting languages, such as pure HTML, Javascript, Ajax, and/or related technologies for managing, viewing, and manipulating images over the web and communicating with a data server. Thus, general graphics/animation services do not include special purpose ActiveX components or Java applets.

Referring again to FIG. 1, the system 100 may include a client device 102 and data server 104 configured to communicate over a network 106. The client device 102 may be embodied as any computing device, mobile or fixed, and may be embodied as a server, desktop computer, laptop computer, mobile terminal, and/or the like configured to communicate with the data server 104 over the network 106. The data server 104 may be embodied as any computing device or plurality of computing devices configured to provide data, such as medical data, to a client device 102 over a network 106 as will be described further herein below. In this regard, the data server 104 may be embodied, for example, as a server cluster, rack of blade servers, and/or may be embodied as a distributed computing system, such as may be distributed across a plurality of computing devices. Although referred to herein as a "server," it will be appreciated that the data server 104 may be embodied as a computing device other than a server. In an exemplary embodiment, the data server 104 may comprise a Picture Archiving and Communication System (PACS) and/or a PACS client. Further, although only a single client device 102 and data server 104 are illustrated in FIG. 1, the system 100 may comprise a plurality of client devices 102 and data servers 104.

Figure 3:
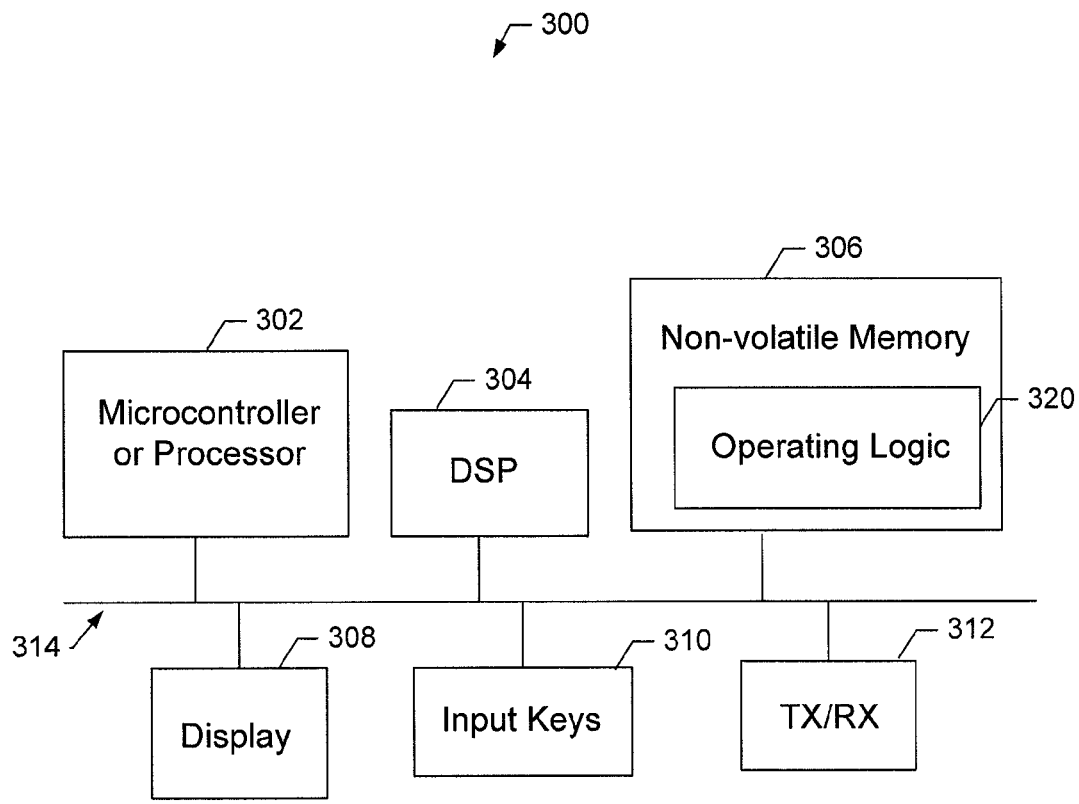
FIG. 3 illustrates a block diagram of a computing architecture suitable for practicing aspects of embodiments of the present invention.

The client device 102 and/or data server 104 may comprise an architecture 300 as illustrated in FIG. 3. In this regard, the computing architecture 300 represents an architecture suitable for practicing aspects of embodiments of the present invention. The architecture 300 may include various means, such as micro-controller/processor 302, digital signal processor (DSP) 304, non-volatile memory 306, display 308, input keys 310 (e.g., 12 key pad, select button, D-unit), and/or transmit/receive unit (TX/RX) 312, coupled to each other via bus 314, which may be a single bus or an hierarchy of bridged buses. Further, non-volatile memory 306 may include operating logic 320 adapted to implement operations for practicing various embodiments of the present invention for managing, viewing, manipulating, sharing, and annotating images in a general purpose viewing agent, such as a web browser. The implementation of the operating logic 320 may be via any one of a number programming languages, assembly, C, and so forth.

Returning to FIG. 1, the network 106 may be any network over which the programmer device 102 and data server 104 are configured to communicate. Accordingly, the network 106 may comprise one or more public and/or private wireless networks, wireline networks, or any combination thereof, and in some embodiments may comprise the internet. The network 106 may further comprise a structured network, ad hoc network, or some combination thereof. The network 106 may further utilize any communications protocol or combination of communications protocols that may facilitate inter-device communication between the client device 102 and data server 104.

The client device 102 may include various means, such as a processor 110, memory 112, communication interface 114, user interface 116, and data viewing unit 118 for performing the various functions herein described. These means of the client device 102 may communicate over a bus, such as the bus 314, and may be embodied as, for example, hardware elements (e.g., a suitably programmed processor, combinational logic circuit, and/or the like), computer code (e.g., software or firmware) embodied on a computer-readable medium (e.g. memory 112) that is executable by a suitably configured processing device, or some combination thereof. The processor 110 may, for example, be embodied as various means including a microprocessor, a coprocessor, a controller, or various other processing elements including integrated circuits such as, for example, an ASIC (application specific integrated circuit) or FPGA (field programmable gate array). Accordingly, the processor 110 may comprise the microcontroller 302 and/or the DSP 304 of the architecture 300. In an exemplary embodiment, the processor 110 may be configured to execute instructions stored in the memory 112 or otherwise accessible to the processor 110. Although illustrated in FIG. 1 as a single processor, the processor 110 may comprise a plurality of processors operating cooperatively and/or in parallel, such as in a multi-processor system.

The memory 112 may include, for example, volatile and/or non-volatile memory, such as the non-volatile memory 306. The memory 112 may be configured to buffer input data for processing by the processor 110. Additionally or alternatively, the memory 112 may be configured to store instructions for execution by the processor 110. The memory 112 may comprise one or more databases that store information in the form of static and/or dynamic information. The memory 112 may store, for example, operating logic for applications, such as, for example, a general purpose viewing agent as well as locally cached data, such as images or other medical data, received from the data server 104. The memory 112 may additionally or alternatively store medical case files, such as may be locally created and/or received from a remote device, such as from the data server 104. This stored information may be stored and/or used by the data viewing unit 118 during the course of performing its functionalities.

The communication interface 114 may be embodied as any device or means embodied in hardware, software, firmware, or a combination thereof that is configured to receive and/or transmit data from/to a network and/or any other device or module in communication with the client device 102. In one embodiment, the communication interface 114 may be at least partially embodied as or otherwise controlled by the processor 110. The communication interface 114 may include, for example, an antenna, a transmitter, a receiver, a transceiver and/or supporting hardware or software for enabling communications with other entities of the system 100, such as a data server 104 via the network 106. Accordingly, the communication interface 114 may be embodied as or comprise elements of the TX/RX 312. The communication interface 114 may be configured to receive and/or transmit data using any protocol that may be used for communications between the client device 102 and data server 104 over the network 106. The communication interface 114 may additionally be in communication with the memory 112, user interface 116, and/or data viewing unit 118.

The user interface 116 may be in communication with the processor 110 to receive an indication of a user input and/or to provide an audible, visual, mechanical, or other output to the user. As such, the user interface 116 may include, for example, a keyboard (e.g., input keys 310), a mouse, a joystick, a display (e.g., display 308), a touch screen display, a microphone, a speaker, and/or other input/output mechanisms. Accordingly, the user interface 116 may be configured to display data, such as medical images, received from a data server 104 and facilitate user interaction with and manipulation of displayed data by receiving from a user of the client device 102 commands and/or queries related to viewing and manipulation of data. The user interface 116 may further be in communication with the memory 112, communication interface 114, and/or data viewing unit 118.

The data viewing unit 118 may be embodied as various means, such as hardware, software, firmware, or some combination thereof and, in one embodiment, may be embodied as or otherwise controlled by the processor 110. In embodiments where the data viewing unit 118 is embodied separately from the processor 110, the data viewing unit 118 may be in communication with the processor 110. In an exemplary embodiment, the data viewing unit 118 may comprise and/or control general purpose viewing agent configured to implement one or more general graphics/animation services. The data viewing unit 118 may additionally or alternatively comprise and/or control a specific purpose medical application, such as, for example, a medical case viewer, a medical image viewer, a medical diagnostic program, a medical diagnostic training program, a medical examination system (e.g., for Continuing Medical Education (CME) credit), and/or the like. The data viewing unit 118 may comprise elements of operating logic 320.

The data viewing unit 118 may be configured to request data from the data server 104. The requested data may be stored remotely in a format in accordance with the Digital Imaging and Communications in Medicine (DICOM) standard data format. It will be appreciated, however, that embodiments of the present invention are not limited to operations using data or images in DICOM format and may operate on data and images in any appropriate format. Further, where reference is made to medical images, it will be appreciated that embodiments of the present invention have applications to other fields as well and thus any type of image may be substituted where a medical image is used for purposes of example. In this regard, the data viewing unit 118 may be configured to send a request for a medical image to the data server 104. The request may be generated in response to actions taken by a user of the client device 102. In this regard, a user may generate a request for a medical image by browsing medical case data, taking medical examinations, interacting with medical teaching files, searching for medical images (e.g., medical images relating to a particular diagnosis, patient demographic, imaging modality, images of a certain part of the anatomy, and/or the like), and/or the like.

The data viewing unit 118 may be configured to receive an image corresponding to the requested medical image from the data server 104. In this regard, the data viewing unit 118 may receive an image that has been processed from a source image by the data server 104. For example, medical images captured by many modalities may often be captured and stored in a relatively low resolution. The data server 104 may process a stored source image corresponding to the requested medical image to generate an image corresponding to the source medical image and having a greater resolution than the source image. This processing may be performed by the data server 104 using a special algorithm so that the higher resolution image is smoothed and pixelization that might otherwise result from enhancing the source image is reduced. Accordingly, data server 104 side processing may be particularly advantageous, as a user of the client device 102 may be able to view the received higher resolution medical image using the data viewing unit 118 and manipulate the received image, such as by zooming in on a section of the image, rotating the image, and/or the like without causing the distortion, blurring, and/or other negative effects that might occur if the user manipulated the original lower resolution source image at the client device 102. For example, general purpose viewing agents, such as web browsers, may be configured to magnify an image to fill a display viewing area. However, general purpose viewing agents may perform this image magnification without processing the image to generate a true higher resolution image and thus a larger, albeit blurrier and more pixilated version of the original low resolution image may result. Accordingly, this data server 104 side processing may facilitate manipulation of the received image at the client device 104 while reducing any blurring, pixelization, distorting, loss of detail, and/or the like that might otherwise result from zooming in on a portion of the image.

In some embodiments, the data viewing unit 118 may be configured to send an indication of a display resolution associated with the data viewing unit 118 and/or client device 102 to the data server 104. This display resolution may, for example, comprise the resolution of a display device coupled to the client device 102, the resolution of a viewing area of an application that may be embodied on and/or controlled by the data viewing unit 118, a display resolution setting of an application or operating system executed by the processor 110, a requested resolution (e.g., user requested, application default, and/or the like) for the requested image, and/or the like. The source medical image may then be processed by the data server 104 based at least in part upon the sent indication of the display resolution. For example, the data server 104 may process the low resolution source medical image such that the resulting processed image received by the data viewing unit 118 may be of a resolution equivalent to the display resolution.

In some embodiments, the received image may be in a different format from the source image from which the data server 104 processed the received image. For example, the source image may be formatted in a DICOM format that is not compatible with the data viewing unit 118. The received processed image may be in a different format, such as, for example, the Joint Photographic Experts Group (JPEG) format, that is compatible with the data viewing unit 118.

The data viewing unit 118 may further be configured to facilitate manipulation of the received medical image by a user of the client device 102. Such manipulation may be facilitated by a general graphics/animation service, such as Flash® that may be included in or otherwise supported by the data viewing unit 118 as previously described. For example, a user may zoom in on the image by providing input to the data viewing unit 118 over the user interface 116. The input may comprise a user selecting to zoom in on the entire image and/or a selected portion of the image using a graphical user interface (GUI) displayed by the data viewing unit 118. Additionally or alternatively, the input may comprise a user dragging a cursor across a display screen, such as with a mouse, horizontally, vertically, or some combination thereof to manipulate the displayed image, such as by zooming in on or panning away from the displayed image.

Manipulation of the image, such as by zooming or magnifying the image, may be limited by the resolution of the image received from the data server 104. In an exemplary embodiment of the invention, if the user wants to manipulate an image beyond the limits of the resolution of the received image and/or beyond some predefined threshold (such as may be defined by a user, coded into the data viewing unit 118, defined by the data server 104, and/or the like), the user may cause a new higher resolution version of the previously received medical image to be processed by the data server 104 from the original source image. In this regard, a user may manually select from a GUI displayed by the data viewing unit 118 to have a new higher resolution image processed by the data server 104. The data viewing unit 118 may be configured to then send the new request to the data server 104 and receive the newly processed higher resolution image from the data server 104. Additionally or alternatively, the data viewing unit 118 may be configured to automatically request a new higher resolution image from the data server 104 when a user attempts to manipulate the previously received image beyond the ranges allowable by the presently displayed image and/or beyond a predefined threshold within the ranges provided by the presently displayed image. In such an embodiment, the data viewing unit 118 may be configured to send the request with an indication of a requested resolution level. The data viewing unit 118 may then receive the newly higher resolution image and replace the existing image with the newly received image so as to allow the user to then manipulate the new image as described previously. Accordingly, the data viewing unit 118 may be configured to seamlessly replace the existing image with the new image so as to provide the user an approximation to a full range of adjustment that would be permissible if the data viewing unit 118 were to locally have access to an image having a sufficient level of resolution to permit manipulation of the image beyond the range of the first received image.

In some embodiments, the requested medical image may be a member of a series of medical images that may be accessed by the data server 104. For example, a requested medical image may be a member of a diagnostic series, a series of images of a single patient, a series of images relating to a certain diagnosis, a series of images captured by a single modality, and/or the like. The data viewing unit 118 may be configured to request the additional images belonging to the same series as the original requested image from the data server 104. This request for the additional images in the series may be a default request that is made whenever a requested image is a member of a series. Additionally or alternatively, the data viewing unit 118 may be configured to make the request in response to user input, such as a user selection of a request for additional images in a series on a GUI provided by the data viewing unit 118. The data viewing unit 118 may then receive the additional images in the series from the data server 104. The received additional images may be in their original resolution and format or may be processed by the data server 104 similarly to the previously requested image. Accordingly, a user may view the series of images together, so that the user may view each image in the context of the series.

In some embodiments, the requested image may be related to other medical images that may be accessed by the data server 104. For example, a related image may be captured from the same patient, related to the same diagnosis, captured using the same modality, captured image of the same body part, have similar patient demographic data s the requested image, and/or the like. The data viewing unit 118 may be configured to request images related to the original requested image from the data server 104. This request for the related images may be a default request that is made whenever a request for an image is made. Additionally or alternatively, the data viewing unit 118 may be configured to make the request in response to user input, such as a user selection of a request for related images on a GUI provided by the data viewing unit 118. The data viewing unit 118 may then receive the related images from the data server 104. The received related images may be in their original resolution and format or may be processed by the data server 104 similarly to the previously requested image. A user may benefit from viewing the related images, as the related images may aid a user in making a diagnosis, such as by comparing a medical image having an undetermined diagnosis to a plurality of related images having a known diagnosis.

In an exemplary embodiment, the data viewing unit 118 may be configured to generate a medical case file from an electronic message, such as, for example, an email message. A medical case file may comprise an application specific file format, such as may be viewed in a medical case file viewer, a medical diagnostic program, and/or the like. Additionally or alternatively, a medical case file may comprise a file storing a medical image and associated information (e.g., diagnostic information, patient demographic information, image attributes, diagnostic attributes, associated text and notes about image and/or diagnosis, and/or the like) about the image. A medical case file may comprise one or more data fields, which may define diagnostic data, medical image modality data, patient demographic data, and/or the like that are associated with the particular medical case and/or medical image. In this regard, the data viewing unit 118 may be configured to receive an electronic message that includes at least one medical image, which may be attached to the electronic message. The data viewing unit 118 may receive the electronic message from a PACS client, such as, for example, the data server 104.

The electronic message may include text data in addition to the medical image(s). The text data may be contained within a subject line of the electronic message and/or a body of the electronic message. In an exemplary embodiment, the text data may be at least partially formatted in a markup language. In this regard, one or more segments of the text data may be delimited by one or more tags that define fields of a medical case file with which each delimited segment of text data is associated. Accordingly, each tag or set of tags may be associated with a particular field of a medical case file and may explicitly associate the segment of text data delimited by the tag(s) with a field. The markup language may be a proprietary markup language used for generation of medical case files from an electronic message or may be a common markup language, such as, for example, hypertext markup language. The data viewing unit 118 may be configured to parse the subject line and/or body of the electronic message to extract the included text data. In embodiments wherein the text data is formatted in a markup language, the data viewing unit 118 may be configured to parse the text data to extract one or more delimited segments of text data and to determine a field of the medical case file with which each extracted delimited segment of text data is associated based at least in part upon the tag(s) delimiting each segment of text data.

The data viewing unit 118 may additionally be configured to parse a header associated with the medical image(s) included in the electronic message. In this regard, for example, the medical image(s) included in the electronic message may be formatted in DICOM format or other format that specifies a header file including data and/or attributes about the image. This header file may describe properties of the medical image, such as, for example, patient demographic information, information about a modality used to capture the image, diagnostic information, and/or the like. Accordingly, for example, the data viewing unit 118 may be configured to parse the header to extract one or more attribute values and/or attribute data from the header.

The data viewing unit 118 may be configured to generate a medical case file comprising the medical image(s) included in the received electronic message. The data viewing unit 118 may be configured to populate one or more fields of the medical case file with text data extracted from the electronic message and/or properties determined from the image header(s). For example, a field of the medical case file may be populated with a segment of text data associated with the field as determined by one or more tags that delimit the segment of text data in the electronic message. The data viewing unit 118 may store the generated medical case file, such as in memory 112.

Referring now to the data server 104, the data server 104 may include various means, such as a processor 120, memory 122, communication interface 124, user interface 126, and/or data provision unit 120 for performing the various functions herein described. These means of the data server 104 may communicate over a bus, such as the bus 314, and may be embodied as, for example, hardware elements (e.g., a suitably programmed processor, combinational logic circuit, and/or the like), computer code (e.g., software or firmware) embodied on a computer-readable medium (e.g. memory 122) that is executable by a suitably configured processing device, or some combination thereof. The processor 120 may, for example, be embodied as various means including a microprocessor, a coprocessor, a controller, or various other processing elements including integrated circuits such as, for example, an ASIC (application specific integrated circuit) or FPGA (field programmable gate array). Accordingly, the processor 120 may comprise the microcontroller 302 and/or the DSP 304 of the architecture 300. In an exemplary embodiment, the processor 120 may be configured to execute instructions stored in the memory 122 or otherwise accessible to the processor 110. Although illustrated in FIG. 1 as a single processor, the processor 120 may comprise a plurality of processors operating cooperatively and/or in parallel, such as a multi-processor system. These multiple processors may be embodied on a single computing device or may be distributed across multiple computing devices, such as, for example, a server cluster, rack of blade servers, or a distributed computing system.

The memory 122 may include, for example, volatile and/or non-volatile memory, such as the non-volatile memory 306. The memory 122 may be configured to buffer input data for processing by the processor 120. Additionally or alternatively, the memory 122 may be configured to store instructions for execution by the processor 120. The memory 122 may comprise one or more databases that store information in the form of static and/or dynamic information. The memory 122 may store, for example, operating logic for applications, as well as medical data, such as images (e.g. DICOM files), that may be requested by and/or provided to a client device 102. This stored information may be stored and/or used by the data provision unit 128 during the course of performing its functionalities.

The communication interface 124 may be embodied as any device or means embodied in hardware, software, firmware, or a combination thereof that is configured to receive and/or transmit data from/to a network and/or any other device or module in communication with the data server 104. In one embodiment, the communication interface 124 may be at least partially embodied as or otherwise controlled by the processor 120. The communication interface 124 may include, for example, an antenna, a transmitter, a receiver, a transceiver and/or supporting hardware or software for enabling communications with other entities of the system 100, such as a client device 102 via the network 106. Accordingly, the communication interface 124 may be embodied as or comprise elements of the TX/RX 312. The communication interface 124 may be configured to receive and/or transmit data using any protocol that may be used for communications between the client device 102 and data server 104 over the network 106. The communication interface 124 may additionally be in communication with the memory 122, user interface 126, and/or data provision unit 128.

The user interface 126 may be in communication with the processor 120 to receive an indication of a user input and/or to provide an audible, visual, mechanical, or other output to the user. As such, the user interface 126 may include, for example, a keyboard (e.g., input keys 310), a mouse, a joystick, a display (e.g., display 308), a touch screen display, a microphone, a speaker, and/or other input/output mechanisms. The user interface 126 may further be in communication with the memory 122, communication interface 124, and/or data provision unit 128. However, in embodiments wherein the data server 104 functions solely to receive data requests from a client device 102 and provide data to a client device 102, the user interface 126 may be limited or even eliminated.

The data provision unit 128 may be embodied as various means, such as hardware, software, firmware, or some combination thereof and, in one embodiment, may be embodied as or otherwise controlled by the processor 120. In embodiments where the data provision unit 128 is embodied separately from the processor 120, the data provision unit 128 may be in communication with the processor 120. The data provision unit 128 may be configured to receive a request for medical data, such as an image from a client device 102. The data provision unit 128 may further be configured to retrieve the requested data from a memory (e.g., memory 122 and/or a remote memory that is accessible by the data server 104) in response to the received request.

In this regard, the data provision unit 128 may be configured to receive a request for a medical image from the client device 102. The data provision unit 128 may then retrieve a source image corresponding to the requested medical image from the memory 122. The data provision unit 128 may be configured to process the source image to generate a second image having a greater resolution than the source image. The data provision unit 128 may perform this processing using a special algorithm so that the higher resolution second image is smoothed and pixelization that might otherwise result from magnifying or otherwise enhancing the source image is reduced.

In some embodiments, the data provision unit 128 may be configured to determine a display resolution associated with the client device 102. In this regard, the data provision unit 128 may be configured to receive an indication of a display resolution associated with the data client device 102 with the request for a medical image and may determine the display resolution from the request. Additionally or alternatively, the data provision unit 128 may be configured to send an explicit request for a display resolution to the client device 102 and may receive a response thereto. The data provision unit 128 may then process source medical image based at least in part upon the sent indication of the display resolution. For example, the data provision unit 128 may process the low resolution source medical image such that the resulting processed image received by the data viewing unit 118 may be of a resolution equivalent to the display resolution.

In some embodiments, the data provision unit 128 may be configured to process the source image to generate a second image having a different format than the retrieved source image. For example, the source image may be formatted in a DICOM format that may not be compatible with software and/or hardware embodied on the client device 102. The processed second image may be in a different format, such as, for example, the Joint Photographic Experts Group (JPEG) format, that may be compatible with software and/or hardware embodied on the client device 102, such as, for example, a general purpose viewing agent.

Once the data provision unit 128 has processed the source image to generate the second image having a greater resolution than the source image, the data provision unit 128 may be configured to provide the second image to the client device 102. In this regard, the data provision unit 128 may send the second image to the client device 102. The second image may then be viewed and manipulated at the client device 102.

The data provision unit 128 may be further configured to receive an indication from the client device 102 of user manipulation of a property of the second image beyond a threshold value. In this regard, a user of the client device 102 may desire an image having an even higher resolution than that of the second image that the data provision unit 128 previously provided. Accordingly, the data provision unit 128 may be configured to receive a request for a higher resolution version of a previously provided image from the client device 102. The data provision unit 128 may then process the source image to generate a third image having a greater resolution than the previously provided second image. In some embodiments, the request for a higher resolution image may include an indication of a requested resolution level and the data provision unit 128 may be configured to process the source image to generate a third image having the requested resolution level. The data provision unit 128 may then provide the third image to the client device 102 to facilitate viewing and manipulation of the third image at the client device 102.

In some embodiments, the requested medical image may be a member of a series of medical images that may be accessed by data provision unit 128. For example, a requested medical image may be a member of a diagnostic series, a series of images of a single patient, a series of images relating to a certain diagnosis, a series of images captured by a single modality, and/or the like. The data provision unit 128 may be configured to receive a request for the additional images comprising the series from the client device 102. The data provision unit 128 may then retrieve one or more of the additional images comprising the series, such as from the memory 122. Additionally or alternatively, the data provision unit 128 may be configured to automatically retrieve additional images comprising a series to which the original requested medical image belongs, such as upon receiving a request for an image. The data provision unit 128 may then provide one or more of the additional images comprising the series of which the original requested image is a member to the client device 102 so that the additional images may be viewed and manipulated at the client device 102. The data provision unit 128 may provide the additional images in their original resolution and format or may process the additional images similarly to the previously requested image.

In some embodiments, the requested image may be related to other medical images that may be accessed by the data server 104. For example, a related image may be captured from the same patient, related to the same diagnosis, captured using the same modality, captured image of the same body part, have similar patient demographic data as the requested image, and/or the like. The data provision unit 128 may be configured to receive a request for images related to the original requested image from the data server 104. The data provision unit 128 may be configured to retrieve related images, such as from memory 122 in response to the request. Additionally or alternatively, the data provision unit 128 may be configured to automatically retrieve images that are related to a requested image.

In an exemplary embodiment, the data provision unit 128 may be configured to determine related images to retrieve based at least in part upon one or more attributes associated with each image. For example, an attribute may comprise diagnostic criteria, such as, for example, patient demographic information (e.g., age, sex, location, and/or the like), information about a modality from which the image was captured, a body part which the image is of, a diagnosis associated with the image, and or the like. The data provision unit 128 may be configured to compare the attributes of a reference image (e.g., the originally requested image) to one or more other images and determine a relevancy of the other images so as to determine related images. For example, the data provision unit 128 may be configured to map the attributes of an image to a coding system wherein an identification code may be extrapolated and a matching score between images may be determined by comparing identification codes of two images. A related image may comprise an image having a matching score above a predefined threshold or may comprise a predefined number of images having the highest matching scores. In this regard, the data provision unit 128 may be configured to determine images related to a reference image through a structured analysis even when an image is not pre-flagged as being related to the reference image.

The data provision unit 128 may be configured to provide the one or more determined related images to the client device 102 so as to facilitate viewing and manipulation of the related images at the client device 102. The received related images may be in their original resolution and format or may be processed by the data server 104 similarly to the previously requested image.

Figure 4:
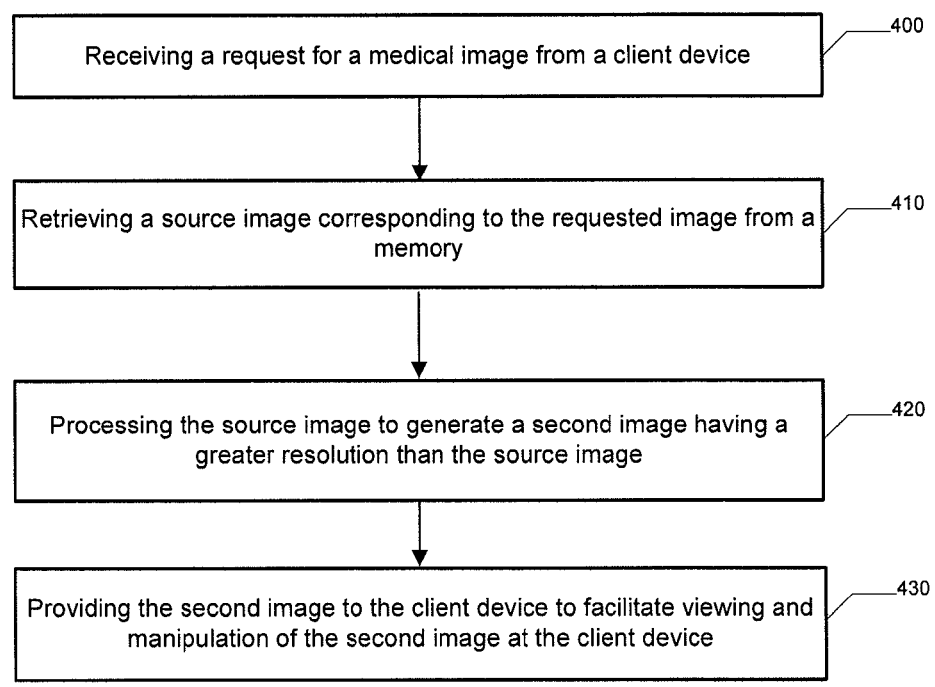
FIG. 4 is a flowchart according to an exemplary method for processing a source image corresponding to a requested image at a data server to generate a higher resolution image and providing the higher resolution image to a client device according to an exemplary embodiment of the present invention.
Figure 5:
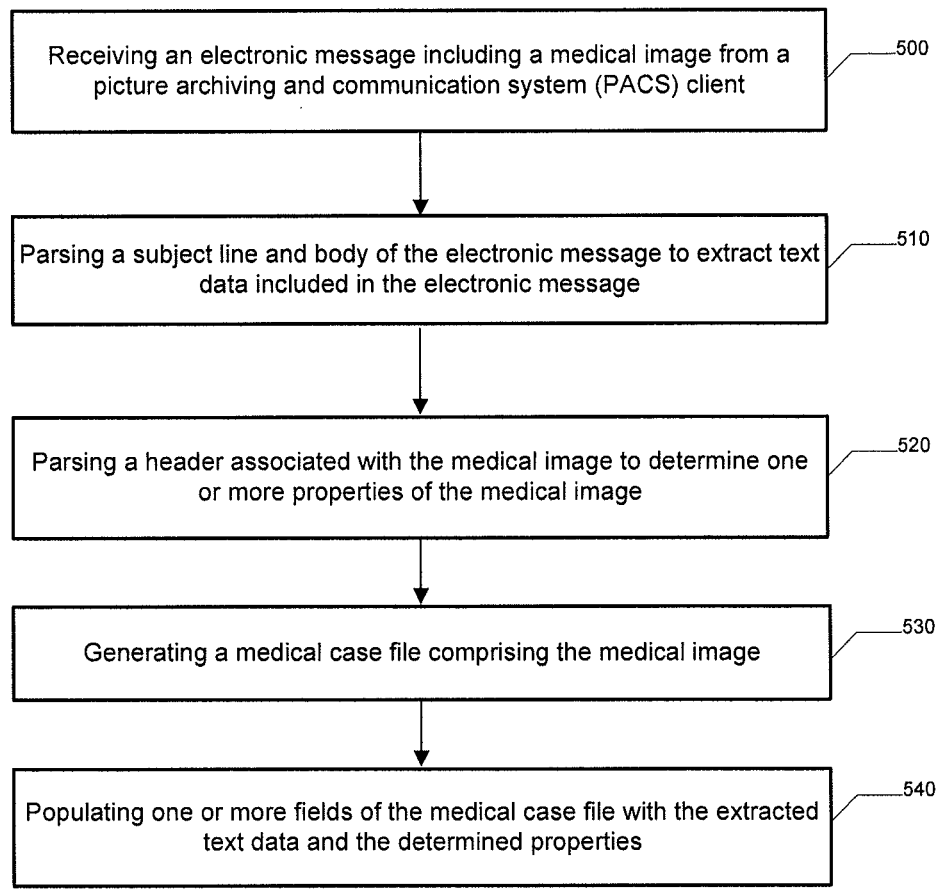
FIG. 5 is a flowchart according to an exemplary method for generating a medical case file from an electronic message according to an exemplary embodiment of the present invention.
Figure 6:
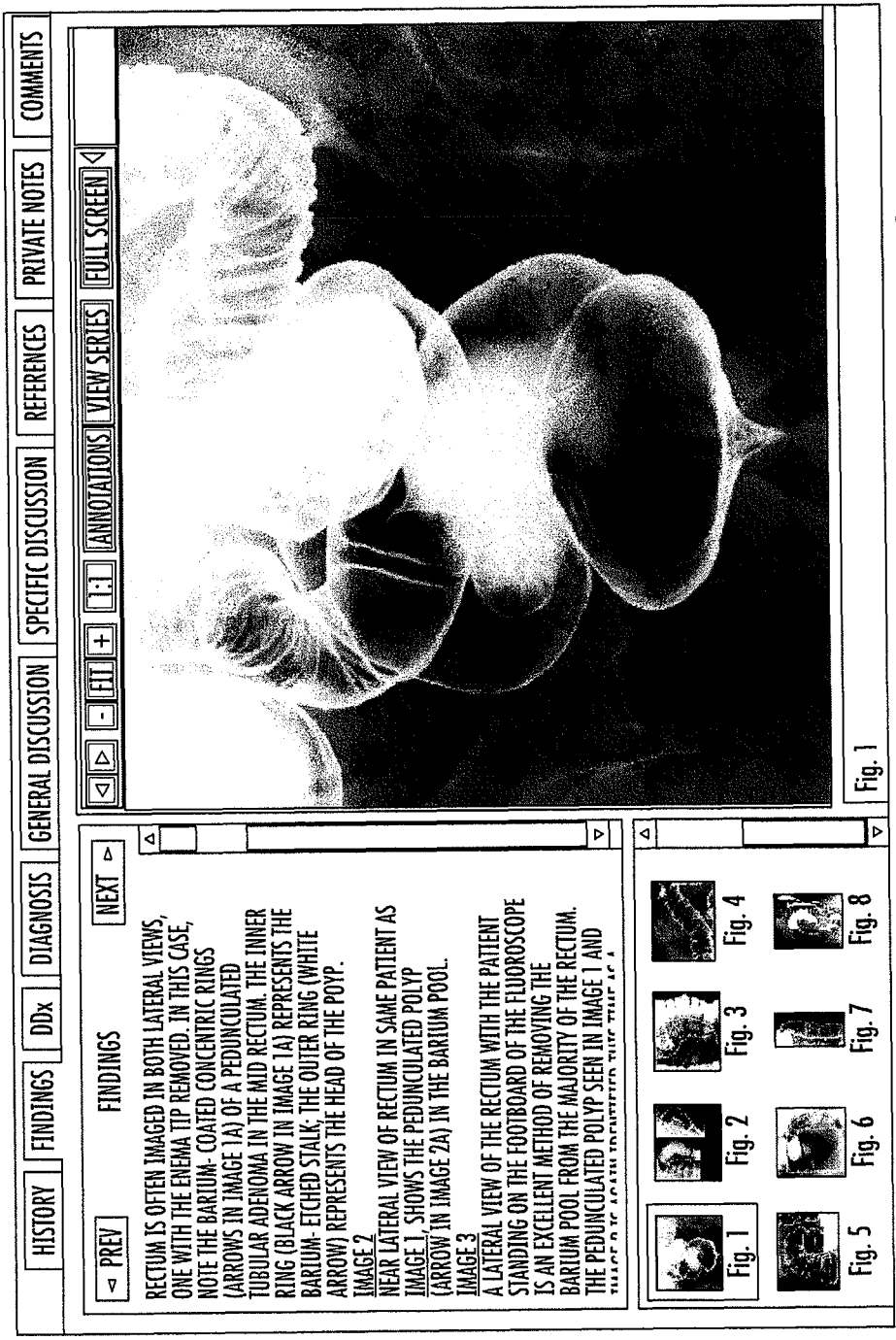
FIG. 6 illustrates a medical case viewer that may be embodied in JavaScript according to an exemplary embodiment of the present invention.
Figure 7:
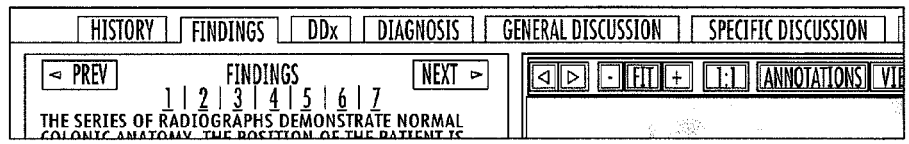
FIG. 7 illustrates a substage navigator according to an exemplary embodiment of the present invention.
Figure 8:
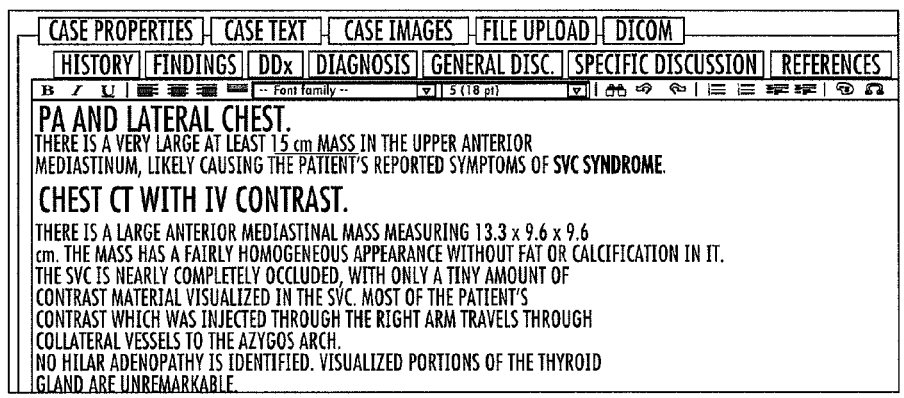
FIG. 8 illustrates a text editor according to an exemplary embodiment of the present invention.
Figure 9:
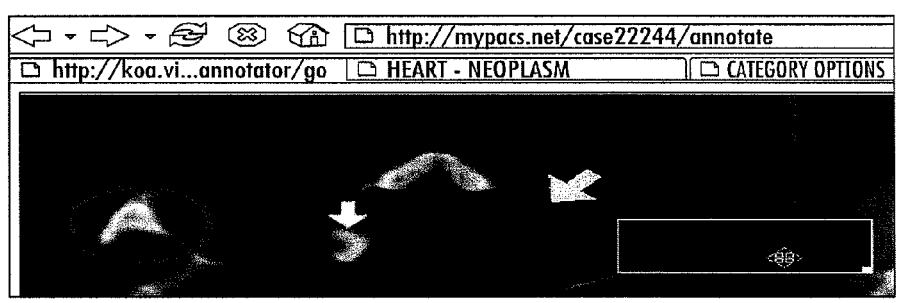
FIG. 9 illustrates an annotator according to an exemplary embodiment of the present invention.
Figures 14, 15:
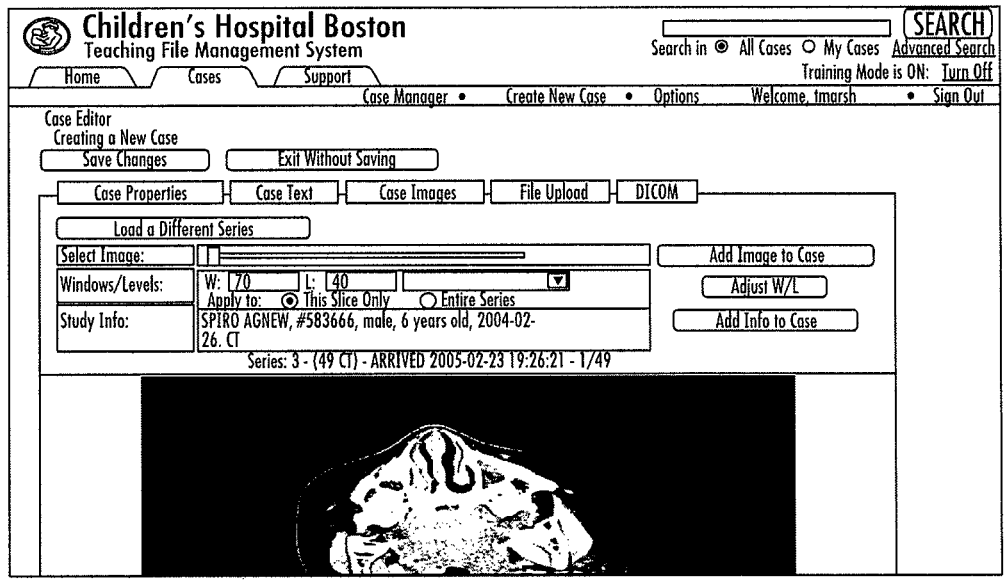
FIG. 14 illustrates a DICOM stack viewer in the editor according to an exemplary embodiment of the present invention.
FIG. 15 illustrates an attribute editor according to an exemplary embodiment of the present invention.

FIGS. 4-5 are flowcharts of a system, method, and computer program product according to an exemplary embodiment of the invention. It will be understood that each block or step of the flowcharts, and combinations of blocks in the flowcharts, may be implemented by various means, such as hardware, firmware, and/or software including one or more computer program instructions. For example, one or more of the procedures described above may be embodied by computer program instructions. In this regard, the computer program instructions which embody the procedures described above may be stored by a memory device of a mobile terminal, server, or other computing device and executed by a processor in the computing device. In some embodiments, the computer program instructions which embody the procedures described above may be stored by memory devices of a plurality of computing devices. As will be appreciated, any such computer program instructions may be loaded onto a computer or other programmable apparatus to produce a machine, such that the instructions which execute on the computer or other programmable apparatus create means for implementing the functions specified in the flowchart block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the flowchart block(s) or step(s). The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

Accordingly, blocks or steps of the flowcharts support combinations of means for performing the specified functions, combinations of steps for performing the specified functions and program instruction means for performing the specified functions. It will also be understood that one or more blocks or steps of the flowcharts, and combinations of blocks or steps in the flowcharts, may be implemented by special purpose hardware-based computer systems which perform the specified functions or steps, or combinations of special purpose hardware and computer instructions.

In this regard, one exemplary method for processing a source image corresponding to a requested image at a data server to generate a higher resolution image and providing the higher resolution image to a client device according to an exemplary embodiment of the present invention is illustrated in FIG. 4. The method may include the data provision unit 128 receiving a request for a medical image from a client device 102, at operation 400. Operation 410 may comprise the data provision unit 128 retrieving a source image corresponding to the requested image from a memory, such as from memory 122. The data provision unit 128 may then process the source image to generate a second image having a greater resolution than the source image, at operation 420. Operation 430 may comprise the data provision unit 128 providing the second image to the client device 102 to facilitate viewing and manipulation of the second image at the client device 102.

FIG. 5 illustrates an exemplary method for generating a medical case file from an electronic message according to an exemplary embodiment of the present invention. The method may comprise the data viewing unit 118 receiving an electronic message including a medical image from a picture archiving and communication system client, at operation 500. Operation 510 may comprise the data viewing unit 118 parsing a subject line and body of the electronic message to extract text data included in the electronic message. The data viewing unit 118 may then parse a header associated with the medical image to determine one or more properties of the medical image, at operation 520. Operation 530 may comprise the data viewing unit 118 generating a medical case file comprising the medical image. The data viewing unit 118 may then populate one or more fields of the medical case file with the extracted text data and the determined properties, at operation 540.

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Example Advantageous Embodiments of the System 100

The above described system may accordingly provide several embodiments that may be advantageous for users, particularly users who may be involved in medical diagnostics. Some of these embodiments are summarized for purposes of example, below.

In one embodiment of the invention, the system may include a tagging system, which allows clinicians to easily assign diagnoses and keywords to reference cases in real time. The tagging interface may be built into the PACS, Radiology Information System (RIS), and/or patient record system, and may be accessible via a button, menu or key combination. The tagger may pop up a text box in which the user types keywords. The system may suggest relative keywords and complete typing, e.g. type "ast" and the system may suggest "astrocytoma". Suggestions may be context-sensitive, e.g., only suggest keywords/diagnoses that are relevant for the given exam context (e.g. if it is a chest exam, don't suggest brain tumors). Suggestions may come from user-defined lists, plus common vocabularies (such as radlex, snomed, umls, mesh, icd), which may be augmented with "folksonomies", suggestions by users (fellow clinicians). Suggestions may be retrieved by searching a knowledge base with the prefix typed in by the user, in real time between key strokes.

Embodiments may further offer a feature in which the system includes diagnosis-centric case organization integrated with third party evidence-based medicine. Each diagnosis may have its own page, whose content is constructed as a "mashup" from content modules that the institution subscribes to (e.g. acr learning files, digitized reference texts, discussions from other institutions). Differentials are listed, and each is a hyperlink to other disease pages and findings pages, each type of finding has its own page, with links to all diseases suggested by the finding. The user is enabled to select a subset of findings to narrow the possible diagnoses. A diagnosis page lists all cases of that diagnosis, which the user can then filter through faceted drill-down (e.g. narrow to specific demographics or anatomic involvement). At each level, the user is presented with a list of differentiators, which when clicked filter the candidate list according to that differentiator. The differentiators are determined by the attribute space. The user may decide what order to perform the filtering by selecting from the attribute space at each level.

Embodiments may further include functionality to support clinician recertification and continuing medical education. In one embodiment, the system may assist in assigning CME credits for time spent using the system. The system will create a Learning Manager (LM) Report which presents in table form (for all users) for a specific date range, details such as how many unique cases each user visited, how many of those cases were viewed with training mode on, and how much total time accumulated during active sessions. The system is managed by privileged users who are able to specify a start date and end date for the report, as well as choose from a popup of preset ranges: [Past Month, Past Year, Entire History]. Various embodiments allow three global settings for tracking visit time, controlled by admin: 1) disabled (do not track visit time), 2) always on (always track everyone's visit times), 3) timer-controlled: only track visit time when user explicitly turns on timer. For the third option, various embodiments provide a "Timer On"/"Timer Off" toggle similar to training mode. To avoid cluttering the screen of users who don't want a timer control, the timer control only appears for users who opt for it. A Preferences screen may allow users to enable or disable the timer toggle for their account. This enable/disable preference and the timer itself will only appear if the admin chooses the global timer-controlled setting.

Embodiments may further offer a feature in which the System, such as through the data viewing unit 118 may enable a user to zoom in on images and pan around in real time. High resolution images may load automatically when zooming in to reveal additional detail. Panning and zooming may be performed using Ajax and/or Flash mechanisms.

Embodiments may further offer a feature in which the system is adapted to enlarge images beyond their native resolution and smoothed on the data server 104 side, so they do not appear pixellated when viewing at high resolution on the client device 102. These enlarged images may be brought in on demand when the viewing space is larger than a threshold, or when the user zooms in beyond a threshold.

Embodiments may include social-collaborative functionality that allows medical images and related information to become focal points for communication and collaboration within and across departments. Functionality includes being able to see which cases are most popular, tagging cases for quick retrieval using dynamic keyword lists, subscribing to Image Alerts in the form of email notification whenever a new case is created that matches their interests, and case-centric collaborative editing interfaces in which authorized users can easily edit content directly in their web browsers.

Embodiments may further offer a feature in which the system includes DICOM series converted for display in a generic viewing agent, such as a web browser, and the stack of images is loaded into a stack viewer, which the user can scroll with a mouse wheel or slider bar. When key images are selected for inclusion in a reference case, the data provision unit 128 may make the entire series available for seeing the context from which the key images came. The series viewer may be embodied as and/or controlled by the data viewing unit 118 and may be integrated into the case viewer, or appear as a popup.

Embodiments may further offer a feature in which the case viewer, which may be embodied as and/or controlled by the data viewing unit 118, is adapted so it can be easily switched between full screen mode and full case mode by clicking a button. By using ajax techniques to hide panels in the document object model, the switch between modes is rapid and does not require the page to be reloaded.

Embodiments may further offer a feature in which image manipulation is controlled by a toolbar which can be collapsed or expanded by clicking on a handle icon on the edge of the toolbar. When the toolbar is collapsed, the image may be automatically resized, such as by the data viewing unit 118, to use the vertical space that was occupied by the toolbar, with just the handle remaining (floating over the image). When the toolbar is expanded, the data viewing unit 118 may resize image so that the expanded toolbar does not obscure the top of the image.

Embodiments may further offer a feature in which image annotations can be turned on or off by clicking on a button on a graphical user interface that may be provided by the data viewing unit 118. Multiple annotation layers may be controlled this way, and they can be labeled, either automatically or through user-defined text labels. Annotations by multiple authors can be distinguished by showing the author's name as part of the annotation label. Annotations may either be represented as transparent layers, or as separate images that are swapped with the non-annotated image.

Embodiments may further offer a feature in which the system enables users to step through iterative case presentation with a convenient interface, similar to VCR controls. The cases may have a presentation mode in which the user simply clicks a centralized "Forward" or "Backward" control, stepping through the case text and full-screened images in a scripted order, thus removing any unnecessary interaction with the individual controls for the cases. The user may click a button to advance or rewind, or may use the scroll wheel or keyboard strokes. An example of an iterative presentation is: show history, show FIG. 1 in full screen, show FIG. 1 caption, show FIG. 2 in full screen, show FIG. 2 caption, show findings subsection 1, show FIG. 3 in full screen, show FIG. 3 caption and annotations, show findings subsection 2, show FIG. 4 in full screen, show FIG. 4 caption and annotations, show differentials, show diagnosis, show discussion, show references, show next case. There may be multiple levels of advancing: 1) next minor step (e.g. subpage or reveal caption), 2) medium step (e.g. next text section), or 3) major step (e.g. next case). This configuration may be useful for training and conference presentation. When advancing steps through the presentation of text in stages, each image may be displayed in turn in full screen mode, with captions turning on after the image is displayed. Case authors may break text into sub pages, which are displayed in stages. Breaking text into sub pages may be achieved with a "page break" button. Authors can also control when images get displayed (e.g. display always, hide until findings stage, hide until diagnosis is revealed, hide until discussion stage). That control can be achieved via dropdown menus. The dropdown menus may be tied together to avoid inconsistencies and preserve image ordering. For example, if the user specifies that FIG. 3 should be hidden until the Findings stage, then subsequent figures will inherit that specification.

Embodiments may further offer a feature in which the system further enables users to adjust window/level settings of images using a dropdown or buttons, or entering in new values manually. The new images may generated on the client device 102 or retrieved from the data server 104.

Embodiments may further include functionality for interdisciplinary collaboration and sharing of content across and within departments, and between institutions.

Embodiments may further include functionality for heterogeneous document management.

Embodiments may further offer Enterprise Groupware functionality, with user-definable roles and policies and fine-grained access control.

Embodiments may further offer a Collaborative Publishing Model, in which users may create, submit, edit, certify, share, and/or annotate cases.

Embodiments may further offer an Ajax DICOM interface with a pure JavaScript/HTML stack viewer and queue manager.

Embodiments may further offer a Document Management System that handles any kind of file, and in particular may handle and/or convert between 100+ types of images.

Embodiments may further offer Intelligent Search & Retrieval, including such features as relevancy ranking and structured queries over any combination of attributes.

Embodiments may further offer Flexible Presentation (including Training Mode (TM)), and Interactivity for CME, Training for Boards, as well as a conference presentation mode for grand rounds.

Embodiments may further offer collection management in the form of hierarchies, shared folders, and tagging.

Embodiments may further offer customizable templates, such as for medical case files, aimed at pathologists, oncologists, cardiologists, and other image workers.

Embodiments may further offer context synchronization, and automated retrieval of similar cases. In this regard, the data provision unit 128 may be configured to retrieve similar cases and/or images based upon attributes of the cases and/or images. Thus, attributes of a reference case or image may be compared to other cases or images to determine similar cases or images. The data provision unit 128 may be configured to use a structured analysis by mapping attributes to a coding system and comparing cases and/or images to generate a matching score, as previously described in the context of medical images.

Embodiments may further offer a video generation service: sequences of images or cine loops can be added to a case (either via dicom or upload), and they will be turned into streaming videos (e.g. Flash) embedded in the case viewer. Such embodiments may be useful for ultrasound and cardiology, as well as other fields.

Embodiments may further offer third party e-libraries to the point of care.

Embodiments may further offer an annotation interface.

Embodiments may further offer multi-resolution zoom.

Embodiments may further offer a smart parser that turns text into hyperlinks that control actions. For example, "Image 2" may become a hyperlink to focus image #2. "Image. 2*a*" may become a hyperlink to focus on the annotated version of image #2. Various synonyms for the word "Image" should be used, e.g. "Figure". Also, reference to another case by case number may automatically become a hyperlink to that case, e.g. "Case 23234".

In one embodiment of the present invention, Ajax and Flash techniques may be leveraged to provide a richer user experience without relying on Applets and ActiveX technology to break out of the limitations normally associated with web-based apps. For example, using these techniques, the system enables users to draw annotations, or zoom in and pan around on images, user interface functionality normally associated with desktop applications or Java programs. Images may be dynamically resized to fit the resolution of the viewing window, and higher resolution images may be automatically retrieved from the server when the image is enlarged. These types of features rely on user interface functionality that is not usually found in pure web applications, e.g. drag and drop, dynamic image manipulation, and instantaneous updates to the current web page without requiring a browser refresh. To circumvent these limitations in web-based software, vendors have traditionally relied Java applets or ActiveX components. However, both of these technologies have major drawbacks, as clinicians and hospital IT staff can readily attest. Java applets suffer from slow downloads, poor performance, and require the bulky Java runtime environment be installed on every client machine. ActiveX components are limited to Internet Explorer on a Windows PC and do not support alternative browsers such as Firefox, or platforms such as the Apple Mac. Furthermore, ActiveX components represent a security compromise, and many hospitals disallow them on diagnostic workstations. Embodiments of the invention may avoid these problematic technologies by employing only pure HTML and JavaScript. These embodiments may rely on a technique known as "Asynchronous JavaScript and XML" (Ajax) to manipulate the browser and communicate with the server asynchronously. Ajax-based solutions offer no compromise in security and ubiquity—they can be run on any hardware/browser combination, without requiring changes to default browser.

Embodiments may further offer a wide range of methods for getting images into a case: DICOM send, file upload, Integrating the Healthcare Enterprise (IHE), Medical Imaging Resource Center (MIRC) publishing, image prefetching, and email. Each PACS may offer its own preferred method for exporting images, so the system can support them all.

Embodiments may further offer the ability to create cases via email, such as previously described. This generation of cases via e-mail may be performed by the data viewing unit 118. From the PACS workstation, users have a menu option to 'email selected images', which opens an email editor with the images attached. They just enter some text and press "send", and the case is automatically created in the teaching file server. The embodiment of the invention parses the email text to create the case title, findings, diagnosis, and discussion, and populates the case with DICOM properties embedded in the images.

Embodiments may further offer the ability to create cases via the IHE Teaching File Clinical Trial Export profile.

Embodiments may further offer the ability to create cases via MIRC publishing.

Embodiments may further offer a streamlined case authoring process that uses image prefetching from a predefined prefetch directory, which may be polled continuously for files by the server. When images are saved to the prefetch directory, they will automatically be imported into the system. Each user may have their own destination directory in the prefetch directory. Images saved to a specific user's directory will be added to cases owned by that user.

Embodiments may further offer a feature in which users may retrieve related cases by clicking on keywords, and anatomy and pathology links, or see a list of all cases with a given diagnosis, or select from a list of findings and see all diagnoses that exhibit those findings, or select from a list of differential diagnoses and see cases matching those diagnoses. The system may use automatic cross-referencing to find key terms and phrases in the text and automatically turn them into hyperlinks to lists of related cases characterized by those key terms and phrases. Key terms and phrases may be identified by full-text parsing of case text and matching against a database of significant terms & phrases.

Embodiments may further offer a feature in which the system enables contributors to edit text using rich text editor, with full control over fonts and formatting. They may insert hyperlinks, bullets, etc. The text editor can be tabs-based with one tab for each subsection. The text editor may be integrated with case viewer, so users with editing privileges may simply click in a text area of the viewer and begin editing the text. When text becomes editable, the viewing window should change color and/or present a cursor to alert the user that they can edit that area. While editing, user may edit case properties through a structured form, and structured values can be selected via checkbox lists, radio buttons, scrollable lists, dropdown menus, or navigating a tree menu.

Embodiments may further offer asynchronous/in situ editing of teaching file content. Any datum of a case that can be represented in hypertext markup language (HTML) (textually-encoded) can be similarly edited and the changes submitted to a web server asynchronously via IFRAME, XmlHttpRequest or Window submission techniques. If necessary, the HTML entities representing the datum can be transformed into HTML form fields or what you see is what you get (WYSIWYG) editors (including plug-in based editors) to be edited and submitted to the web server.

Embodiments may further offer a feature in which the system enables content to be protected from piracy using browser cache management.

Embodiments may further offer a feature in which the system inserts watermarks into images as a piracy protection mechanism.

Embodiments may further offer a feature in which the system automatically logs out user sessions after an expiration interval.

Embodiments may further offer a feature in which logins can be integrated with hospital single-sign on, either via Lightweight Directory Access Protocol (LDAP), WSL, or some other mechanism.

Embodiments may further offer a feature in which the system enables users to save searches and re-execute saved searches with a single click.

Embodiments may further offer a feature in which the system enables users to sign up for email alerts. Whenever cases matching their saved search criteria are created or modified, the user will receive an email with a link to the case(s).

Embodiments may further offer a feature in which the system enables contributors to solicit comments or assistance through a form element and other users who have subscribed to alerts will receive notification that a new case is awaiting their feedback, and they may add comments directly to the case and/or email the author.

Embodiments may further offer a feature in which the system enables users to practice on random cases in unknown mode. A button on a GUI may retrieve a random case that the user hasn't seen before. Users may constrain the random case to specific properties, folders or categories.

Embodiments may further offer a feature in which multiple accounts may own the same case. The original author may select additional owners or authors of the case. Authors are the named users who are credited with authoring the case, whereas owners are the accounts that control the case.

Embodiments may further offer a feature in which case collections (saved searches, folders, etc) may be assigned RSS feeds, e.g. "case of the day" can be served as an RSS feed.

Embodiments may further offer a feature in which the system enables users to be able to add their own structured attributes to cases to support their unique requirements.

Embodiments may further offer a feature in which the system enables users to assign their own drill-down anatomy and pathology hierarchies, or import a standard like RadLex.

Embodiments may further offer a feature in which there can be multiple access-controlled DICOM queues. Each queue may be assigned to a user or group. It is feasible for each user to have their own queue, or each subspecialty group. Queues can be differentiated by AE_TITLE and/or port number.

Embodiments may further offer a feature in which the system enables key images to be added to a case with a single click. DICOM header info may be automatically copied into the case.

Embodiments may further offer a feature in which the system automatically reclaims disk space wherein unused DICOM series are freed up after an expiration interval.

Embodiments may further offer a feature in which the system includes a graphical user interface to provide all DICOM configuration and maintenance functionality. An administrator may see at a glance which DICOM studies are used in cases.

Embodiments may further offer a feature in which the system includes an ontology alignment tool to convert between two arbitrary coding systems, e.g from ACR codes to another coding system, using some form of declarative mapping. This will be useful for import projects like Dr. Banner's cases, as well as for migrating customer systems from an old category system to a new one, and ultimately for doing queries across divergent category systems.

Embodiments may further offer a feature in which the system enables users to drill down to cases via anatomy and pathology, or via folders. At each level, the number of cases for each sub-branch are indicated in parentheses (magnitude indicators).

Embodiments may further offer a feature in which search results may be ranked using intelligent ranking, with the most relevant cases listed first. Relevancy may be determined by exactness criteria on search terms, and some fields are rated higher than others (e.g. title, diagnosis, keywords are all higher than discussion).

Embodiments may further offer a feature in which the system enables users to turn on "training mode" to view cases as unknowns. When training mode is on, abstracts/listings do not reveal title or diagnosis, and in the case viewer, case text and captions are revealed iteratively instead of all at once.

Embodiments may further offer a feature in which the system enables users to define their own custom attributes. Attributes are assigned a label and a type. The type may be a standard type (free text, date, number, Boolean) or map to a structured vocabulary. Type may also specify a form element to be used and cardinality (many, single). Users may create new vocabularies and assign them names, to be re-used for multiple attributes. Attributes may appear in the editor and search forms. Attributes can be scoped by group, and users may "subscribe" to various attribute groups, having those attributes appear in the case editor.

Various embodiments, as described above, or otherwise, can exhibit some or all of the following innovations:

Content Viewer Innovations

Asynchronous HTTP submission: a submission of data via HTTP not requiring the originating webpage to refresh its contents or be redirected to another location. If a relevant response is generated from the processing of the submission, the originating webpage (or any other related webpage) can be updated programatically without need for fully refreshing its contents or being redirected to another location.

In situ "WYSIWYG" text editing: editable text areas allowing the user to add format and style to their text input and having that style and formatting may be reflected immediately in the text area.

Tabs-based content display: the content of a viewport may be controlled by the clicking of various labeled tabs, each tab presenting associated content. The content can be forms, which can be submitted either synchronously or asynchronously. An additional tab/button can submit all tabs/form content in a predefined order.

Annotated image swapping: in situ client-side swapping of images controlled by a hyperlink or button, e.g., replacement of an image with a similar image highlighting important/relevant information or changes.

AJAX search: asynchronous submission of a search query allowing the display of previous results until new results have been returned and presenting the results in an optionally scrollable hierarchical representation, which allows for a compact representation of the entire result set that can be expanded by selecting a particular level of the hierarchy until a final result items are revealed.

Asynchronous window/level adjustment: an explicit (arbitrary or context-dependent) or implicit (referring to context-dependent parameters) window/level settings for an image/image set are selected and submitted asynchronously to a remote imaging service. The images may be returned asynchronously as available and replace the respective original image(s) in the image (set).

Image set viewer: an image set may be viewed one image at a time and controlled either via GUI widgets and/or mouse or keypress events. The images are loaded asynchronously so that the set can be viewed in a partially loaded state (e.g., displaying only those images that have become available).

Automatic metadata inclusion: automatic inclusion of file metadata to an aggregation when that file is added to the aggregation. Any client-side representation of the aggregation is updated instantly, e.g., inclusion of DICOM header information upon addition of a DICOM file to a teaching file.

Resizeable window divisions: window divisions that are dynamically resizable via drag-and-drop operations and/or window resizing events. Certain divisions may be deemed to be of fixed size or proportional to another and may only be resized within predefined limits or dynamically calculated contextually-based limits.

Control toolbar overlay: a set of controls superimposed over another entity may be minimized, moved and/or hidden optionally. The controls may be located outside of the boundaries of the entity when maximized and the minimization process may resize the entity and superimpose the controls.

Asynchronous message posting: messages related to an entity can be created and/or edited via a form and asynchronously posted. The new and updated messages may be displayed immediately.

Object highlighting: objects of certain criteria may have multimedia effects applied to them when a user positions the cursor within their vicinity, suggesting their relevance/applicability/candidacy/etc. For a particular action/operation; attach an event listener to the mouse events for a particular HTML object that triggers the relevant multimedia effect (eg: adding a colored border around the object or changing the color of the existing border, so as to draw attention to it while the cursor is over it).

Image zooming and panning: viewed through a statically sized (but independently resizable) viewport, an image can be magnified or demagnified and repositioned by drag-and-drop, button and/or keypress events; an IFRAME element can be used as a viewport, wherein an image is the single significant element within that window. Using a drag-and-drop toolkit (such as Yahoo's YUI), the image can be moved around within the window, but may be automatically clipped by the browser to the dimensions of that IFRAME. the image can be magnified via JavaScript by adjusting the width and height proportionally in relation to the original dimensions of the image. The drag operation may be nullified if the destination of the image would place any of its boundaries within the boundaries of the viewport, thereby constraining the drag operation to display only the image contents within the viewport (and not any margins outside the image).

Dynamic image resolution: an image that has been magnified beyond a predefined or dynamically calculated contextually-based threshold may be substituted in situ with a higher-resolution rendering of the same image; once an image has been magnified beyond its native dimensions, it can be replaced by a higher-resolution rendering of the same image. This can be done either ad hoc, by means of either a pre-existing URL, or an AJAX (IFRAME or XmlHttpRequest) request to a URL-based web service that supplies the URL for the replacement image, optionally creating the image at that URL on-demand.

Fitted object sizing: an object may be dynamically resized to the size of its container when that container is itself resized (e.g.: an image will be resized to the size of its parent window or container when the parent is resized). Whenever an event occurs which changes the size of the container, whether it be the user dragging the borders of the container, or the browser window itself being resized, JavaScript may be used to calculate the new size of the container and then set the width & height properties of the image in the document to fit the new container size—unless the image has already been manually zoomed in, in which case the image may not be resized until the user clicks the Fit button.

Hover menus: hidden menus that appear when the cursor is positioned over a particular target that allow various actions to be made either synchronously or asynchronously.

Lookahead data loading: when accessing a member of any set of data, the remainder or any subset of that remainder of the data set may be asynchronously loaded via AJAX techniques to remove access latencies associated with on-demand data loading. An example of this would be asynchronously pre-loading the remainder of search results for instant access when accessing any particular search result in a result set or asynchronously pre-loading the images of a teaching file regardless of how many images can be viewed simultaneously.

Integrated DICOM stack viewer: if an image within a teaching file originates from a DICOM series, the remainder of the images in the series may be made available by the data provision unit 128 to replace the currently displayed image. The images of the series may be pre-loaded (such as by the means described in "lookahead data loading") and a set of widgets (buttons, hyperlinks, sliders, etc) may be provided, in addition to keypress and mouse events, to control the currently displayed image, simply replacing the source attribute of the image with the URL of the replacement image. The pre-loading scheme combined with a in-memory buffering system wherein references to JavaScript Image instances (referring to the URLs of the images in the series) are created and maintained will ensure that the replacement of images will be of the most minimal latency.

Pop-up DICOM stack viewer: if an image within a teaching file originates from a DICOM series, the remainder of the images in the series may be available to replace the currently displayed image. The series may be viewed in a separate window, rather than in situ, as described in "integrated DICOM stack viewer"; the implementation of this is nearly identical to "integrated DICOM stack viewer," except that a window may be created in which the image is displayed and updated (rather than being updated in situ).

Printer-friendly mode: the content object will have a display mode optimized for printing, either outputting a Portable Document Format (PDF) file or a plain HTML file with printer-friendly dimensions. The printer-friendly display may be constructed using any combination of cascading style sheets (CSS) media selectors, Extensible Stylesheet Language Transformations (XSLT), dynamic HTML (DHTML) markup, and JavaScript scripting.

Resizable images: dragging on any image (especially thumbnail images) to grow or shrink the image size if the image is a member of a collection that is displayed (such as thumbnail renderings of the images of a case). All members of that collection may be resized to the dimensions of the manipulated image, either dynamically or upon completion of the resizing operation on the manipulated image.

Permission/rule-based drag and drop in browser: attach events to document object model (DOM) elements' mouseover event. While dragging DOM elements, compute intersection of elements and compare to a static JavaScript Object Notation (JSON) representation of intersection rules. If session configuration indicates permission to drag element over the other element, signal by changing the appearance of the dragged image with decoration (i.e., red border for no, green border for yes, "X" background for no) to signify whether or not the user are allowed to drop the item. When mouseup event is fired, consult same rules to verify that user has permission to drag. Similarly, re-enforce rules on the backend to prevent users from communicating drag event to server from some other application.

Creating dynamic attributes in web-based application: while selecting styles for attributes (dropdown, radio, free text, text area, etc) events are fired that may cause an asynchronous update of a hidden iframe embedded in the application page. The iframe may contain the very same template that is later used to render the attribute, thus providing the user with an exact representation of the future attribute.

Web-based Distributed Authoring and Versioning (WebDAV) access to an object database with access control: create an interface between back-end framework (i.e., Catalyst) and incoming hypertext transport protocol (HTTP) traffic. Interface may be responsible for translating all incoming DAV requests into corresponding object accessors. Permissions from objects may be translated in reverse to DAV error messages indicating whether or not a user is allowed to access the object. Furthermore, interface may allow for translation of file names into arbitrary names, giving the user the appearance that they are seemlessly interacting with a file system when they are truly querying a relational or object database.

Live upload & download indicators in browser without plugin: upload indicator—when a user has selected multiple files for upload, an event may be attached to the form submission such that when the form is submitted, a dynamic iframe appears on the page which polls server with a small (1-5 second) period to see what the status of the temporary file being uploaded is. This status may be displayed on the webpage giving the user an indicator of their upload progress. This is a completely novel application of AJAX. A timeout may also be setup upon form submission so as to periodically verify that upload is still in progress (computed by comparing browser and server side checksums), alerting the user if it is interrupted for any reason. A Download indicator may also be provided in browser without plugin and may be embodied as a hidden iframe with periodic polling to server updates a DOM element that represents the state of the downloaded object.

Integrated case editor: The case can be edited directly from the viewer. This provides a "WYSIWYG" editor, which is more convenient than a separate editor. When viewing a case that is editable by the user, all text fields may be replaced with editable regions when they are clicked (using JavaScript). These editable regions may include clickable text tabs such as "Findings" as well as image captions. Additionally, a "Case Properties" tab may appear in the case viewer, for editing properties.

Next to the thumbnails appears a button for uploading images, which pops up an upload form. Uploaded images may immediately appear as thumbnails. Another button may pop up a form to add images from the DICOM queue(s).

Display of images may be controlled as follows: each text section exhibits a selector (e.g. checkbox) in the upper right corner of each thumbnail. Activating the selector means that the corresponding image should display during that stage (or subsection). Furthermore, thumbnails may be dragged and dropped to reorder image sequence, or dragged to a trashcan for deletion.

Auto image focusing: if training mode (TM) is on, when switching to a new text section, if new thumbnails appear, the image pane may be automatically focused on the first new image. This will call extra attention to the new images, and save the user the step of having to click on a new thumbnail. However, it may have the drawback of something unexpected happening.

Case comparison viewer: from search results list, user can select a bunch of cases using checkboxes, and then click "Compare Cases". This may load all the selected cases in a single modified version of the case viewer without tabs. Three panels may be displayed with the thumbnail panel in the upper left hand position (e.g., above text panel instead of below). Show ALL thumbnails of all loaded cases, labeled FIGS. 1.1, 1.2, 1.3, 2.1, 2.2, etc. The case text panel (lower left) may show all the case text associated with the case of the currently displayed image. Case text may be concatenated into a single scrollable pane, starting with title and history (similar to how it appears in the classic viewer). The data viewing unit 118 may enable scroll wheel or slider for the right-hand panel, allowing user to treat all the combined images as a stack. The idea is that users may quickly scan up and down through all the case images until they see one that looks like the subject they are trying to diagnose.

Enhancement: allow the user to split the right-hand panel into a grid of 2 or 4 image panels, each of which can be an independent "stack viewer" of case images. Click one of the grid squares to focus that sub panel, then scroll that sub panel independently, to be able to see selected images side-by-side.

Manual merging of cases: from the bottom of search results list, or case listing in folder, next to the link "copy one or more cases to a folder", add another link "merge cases" similar to the "copy cases" function, it may bring up a list of cases with checkboxes next to each, with instructions "Select cases to merged using checkboxes below, and then press [Merge Selected Cases]." Submit the form to see a new form listing the cases to be merged, with a radio button next to each, and instructions: "Specify the destination case and press [Merge Cases]." Beneath the submit button should be a checkbox (default=checked) saying "Delete source cases after merge." When pressing submit, if "delete source cases" is selected, prompt the user with "Is the user sure?" Then perform the merge and delete the originals (or not).

Merging may result in the destination case being augmented as follows: add images from all the other cases. If the source cases are being deleted, the user can reuse the Case Image objects, otherwise the user can copy the images. Be sure this is compatible with the [used] feature of the DICOM queue be sure to also copy captions. Text fields: append values of text fields from all the source cases; separate appended text with new lines. Avoid duplication of text: if a text field is identical to a previously appended text field, skip it. Case properties: add modalities from sources to destination case. All other fields may be ignored.

Case lookahead loading: when viewing a case, after loading all its images, load the next case and all images in the background;

Magnifying glass to view a portion of the image larger without zooming in;

Private notes: should be a text area that is always editable and displays the viewing user's private notes for the case; let all users make their own private notes on any case, not just the author; editor will open in a new window and when clicking save changes the case viewer will automatically update; when holding down mouse button to move image the pointer should change to a different icon td signify when panning.

Integrated DICOM stack viewer: if a stack is available for a case image, provide a stack-slider in the image button panel, allowing the user to scroll through zoomed-to-fit stacks without a new popup window.

Slideshow mode: have a presentation mode in which the user simply clicks "Forward" or "Backward", stepping through the case text and full-screened images in a scripted order, taking away any need to "think" about where to click next.

Printer-friendly mode: have a display mode optimized for printing, either outputting a PDF file or a plain HTML file with printer-friendly dimensions.

Resizable thumbnails: click drag diagonally on any thumbnail to grow or shrink the thumbnail size. All thumbnails, such as in a series of images, may be simultaneously resized, such as by the data viewing unit 118 and/or data provision unit 128. Some Embodiments May Contain The Following Features:

DICOM query/retrieve client interface: May allow users to query/retrieve DICOM studies from DICOM sources such as the PACS. The "search for series" interface in the case editor may allow the user to search available DICOM servers as well as the Teaching File (TF) queue. The client interface may use query/retrieve to submit the query to the selected sources, then show the results list from each source. The user can retrieve a series from an external source by clicking on it. This will retrieve the images via query/retrieve, import them, convert them to jpegs, and load it into the browser all in one step. There should also be an admin option that allows the admin to specify DICOM sources (address, port, AE_TITLE).

Hierarchical ontology editor: An interface may allow users to define custom attribute hierarchies (e.g. anatomy, pathology, etc) and structured keyword lists for annotating cases. The customized attributes will then appear in the case authoring, editing, and retrieval interfaces. Category editor interfaces may look a lot like folder editors. The interface may include the following operations: view category, delete category, rename category, move category (move it to a different place in the hierarchy), add subcategory, merge category to another category.

In one embodiment, a special group (e.g. "Category Editors") may exist whose members are allowed to edit the category hierarchy.

In one embodiment, each top level category of the pathology tree may be associated with a specific top level category of the anatomy tree. This is used to control a context-sensitive popup when assigning pathologies to cases. When editing a top level pathology category, the interface may allow users to specify which top level anatomy category the pathology category is associated with. When creating or editing a case, or when performing advanced search, there may be at least three popup menus: Anatomy, Specific Anatomy, and Pathology. The latter two popups will depend on the selected value of the Anatomy popup. Anatomy: [popup of top level anatomy categories only]; Specific Anatomy: [popup of subcategories of chosen anatomy category, arbitrarily deep]; Pathology: [popup of subcategories of Pathology associated with chosen top-level anatomy category].

Age/gender display: context-sensitive omission: if History text mentions the patient's age and sex, the interface can omit redundant display of patient age & sex in the history tab. For example, if one of the following space-separated words exists: old, year-old, y.o., yo, y/o and one of the following exists: male female man woman then omit the redundant age and gender display.

Save case histories: keep a history of all edits to cases. One way to do this is to create two tables: MedCaseHistory and CaseImageHistory these may be identical to MedCase and CaseImage, with two added columns to keep track of the user making the change and the date-time of the change. Whenever a case is saved (including initial creation), store a copy of it in the MedCaseHistory and CaseImageHistory tables (copy every field including OIDs), Another approach would be to store only the differences from the prior version of the case.

Automatic space reclamation (enhanced auto purger): have an automated procedure to reclaim disk space when the disk reaches a predetermined capacity (X %). In one embodiment, first clear out studies which are not associated with any case images. Clear them out in the order of studies least recently PUSHED to the DICOM queue. Do not clear out any studies which were pushed within the past 48 hours. Clear out the DICOM images as well as the jpeg images that were created from them, and all associated repo objects in the database.

In another further embodiment, if the disk is still not 5% below the threshold, start clearing out studies which are associated with case images. Clear them out in the order of cases that were least recently VISITED by end-users. For these studies, do NOT clear out the associated JPEG images (just clear out the DICOM images). Case visitors will still be able to view the stacks behind the case images, but they will lose the ability to adjust the windows/levels.

In another embodiment, once every N hours, check disk usage. If it is higher than X %, send an email alert to the admin, and clear out DICOM series until usage goes down to Y %. use a procedure such as the following to reduce disk usage. Check disk usage after every stage and stopping when usage falls below Y %: clear out all unused series that are over a week old; clear out all unused series that are over 1 day old; clear out all USED series which take up lots of space if the cases have not been visited in a long time; clear out all USED series which take up lots of space if the cases have not been visited recently; clear out all USED series regardless of size if the cases have not been visited in a long time; clear out all USED series regardless of size if the cases have not been visited recently. An admin option can enable or disable this script, and specify the thresholds (90%/80%) and specify values for "recently", "long time", and "lots of space".

PowerPoint importer: may allow users to submit cases via PowerPoint presentations. use win32::ole to parse the contents of the presentation. Create one case per presentation. Create a case image for each image in the presentation. If a slide contains an image and some text, use the text as the caption. If the slide contains multiple images and text, try to figure out which images should get captions if the user can think of a way to do this, or just combine all the text as the caption of one of the images. If a slide contains only text and no images, stick the text in "discussion" (discussion will contain concatenated text from multiple slides). The PowerPoint importer may further try to preserve some of the text formatting (bullets, etc) as HTML within the discussion text, but this is not a strict requirement if it is hard to accomplish. In one embodiment, the title of presentation (or text of first slide) becomes title of case, and slide text converted to case fields if easily parseable.

PowerPoint exporter: Allow users to export their cases as PowerPoint presentations. In one embodiment, the conversion is done on the server, and the user can simply download the PPT file. In another embodiment, a client-side executable may convert exported case content (in mire format or other format) into PPT. Automatically extract content from any container (e.g. a zip file), convert the text content and images into a PowerPoint file, save the new PPT to a default location, and then automatically launch PowerPoint on the presentation. Default of one image per slide is reasonable, and allow user to control how many images appear per slide. The server that generates mirc-ppt can include an optional directive which will contain parameters for the user's converter, e.g.: <display-parameters>; <images-per-page>2</images-per-page>; </display-parameters>.

Images may be resized if they are too large, so they always fit on the slide. The image size may depend on how many images are on a slide. Also, the font sizing may be handled such that the font may be decreased in size if necessary to fit all text on the slide.

In one embodiment, the feature can allow exporting multiple cases at once, either into a single presentation or multiple presentations. For example, handle a zip file that contains multiple XML files. A "table of contents" slide is created that lists all the cases, then append the output of each case to the presentation.

Quiz Authoring, Viewing and Tracking

Allow case authors to attach multiple choice questions and answers to their cases. Keep track of users' performance when they take quizzes. Allow instructors to lock certain cases as unknowns for specific users until quizzes have been performed.

A quiz is a set of questions, each of which consists of the following attributes:
    Question sequence number
    Question prompt (text)
    List of answers
    Answer sequence number
    Answer correctness (correct/incorrect)
    Answer explanation (optional text to appear after the user has selected that answer)

Creating/Editing Quizzes:

A link to case editor prompts user to Add Quiz or Edit Quiz. Clicking on this launches the Quiz Editor. The form contains a question prompter:
Prompt: [textfield]
Answers:
    Answer # [textfield] Popup[correct/incorrect] Prompt: [textfield]
    Explanation: [textfield]
    (repeat the answer prompt several times)
[Add New Question]

Pressing button to Add New Question creates the question and then reloads the form, prompting for a new one. Existing questions should appear beneath the new question prompt, with each question and answer set having their own form elements with the fields filled in, followed by a [Submit Changes] button at the very bottom of the form. Each question prompt should include a Question # textfield that can be edited to reorder questions (similar to how case images have sequence numbers in the case editor) Also each question should have a link next to it add more answers which creates some extra blank answer slots under the question (using JavaScript or form reload).

Viewing Quizzes

Cases with quizzes are visually identifiable from the case abstract level (e.g. marked with a quiz icon). When Training Mode is turned on, if a case has a quiz, the training mode navigator (at the top of the case) prompts user to Take Quiz. When user takes quiz, reload the case view with the first quiz question appearing under the images (in a section labeled Quiz):
    Question 1: prompt-text
A. answer-text
B. answer-text
C. answer-text The answer letters are hyperlinks. If the user clicks on the wrong answer, reload the page with text in the quiz section, e.g.:
    Question 1: prompt-text
        The user chose: A. answer-text
        Sorry, that's WRONG.
        Explanation-text
        <try again>

If the answer is right, display a different message in the quiz section, e.g.:
    Question 1: prompt-text
        The user chose: B. answer-text
        CORRECT!
        Explanation-text
        <next question>

When the user has correctly answered all the questions, finish with a message, e.g.:
    Congratulations! The user have completed the quiz.

And repeat the training mode navigator at the bottom of the case.

If training mode is not on, have a link Take Quiz appear at the top of the case, which will turn training mode on and go directly to the quiz stage.

Keep track of which quizzes a user has completed (using a mechanism similar to the visit tracker). If a user has completed a quiz, use a different icon in the case abstract than if the user has not completed a quiz. Also, display the date/time that the quiz was completed by that user.

Other embodiments may include these additional features:

Support the creation of multiple quiz sections which can be assigned to different stages of training mode (e.g. have one set of questions occur before findings are revealed and another set of questions occur after findings are revealed.)

Allow authors to lock cases so the quiz must be taken before the full case is revealed.

Allow interleaving of quiz questions and display of images.

Custom Attribute Manager

Under Options, admins may have access to the following additional System Commands: Manage Custom Attributes Options>Manage Custom Attributes Show a table of all the custom attributes, including their Name, Type, whether or not they allow Multiples, and what is the preferred Form Field. Possible types are Text, Date, Boolean, Number, or Vocabulary.

Vocabulary names are not required to use capital letters.

Every attribute should belong to an attribute group. Case authors may add attribute groups to their cases. there should also be a way to add a new attribute group (just name it).

When displaying the table, if a Type is a Vocabulary, just show the Vocabulary name, e.g.:

| Name | Type | Multi-ples | Form field |
| --- | --- | --- | --- |
| Language | LANGUAGES | No | dropdown menu |
| Primary DX | PATHOLOGIES | No | dropdown menu |
| Other Dx | PATHOLOGIES | Yes | multi-select dropdown menu |
| Stained | YES/NO | Yes | radio buttons |
| Procedures | PROCEDURES | Yes | checkboxes |
| Magnification | Text | N/A | narrow text field |
| Special Keywords Text | | N/A | wide text field |
| Differential | Text | N/A | text area |
| Recruit Date | Date | N/A | date |

To edit or delete an attribute, click on its name.
Also display links for:
    Add New Attribute
    Reorder Attributes
Options>Manage Custom Attributes>Add New Attribute
Name: [textfield]
Group: [dropdown containing attribute groups]

Type: [dropdown containing all vocabularies, plus Date, Text]
Multiples: [radio buttons for true or false]
Form field: [context-sensitive dropdown containing possible choices based on type, as follows:]
  If Type=Vocabulary & Multiples=True:
multi-select dropdown menu, checkboxes
  If Type=Vocabulary & Multiples=False:
single-select dropdown menu, radio buttons
  If Type=Date:
date
  If Type=Text:
narrow text field, wide text field, text area
[Submit: Create Attribute]

Options>Manage Custom Attributes>Edit Attribute
Editing Attribute:
Name: [textfield]
Type: [dropdown containing all vocabularies, plus Date, Text]
Multiples: [true/false radio button]
Form field: [context-sensitive dropdown containing possible choices based on type]
[Submit Changes] [Delete Attribute]
If changing type, warn user:
  Changing the type will cause all existing cases to lose their current value for this attribute. A prompt may appear asking, "Is the user sure the user wants to do this?"
  If changing a form field from multi to single (e.g. from checkboxes to radio buttons), warn user: "Changing the form field from multi to single may cause cases with multiple values assigned to that field to lose some of their values. Is the user sure the user wants to do this?"
Case Edit Modifications:
  Once a new attribute has been created, it may appear in both the case view and case edit pages. Also, the attribute must be searchable.
  1. View: additional attributes should appear in the additional details section in alphabetical order right before Case. An example of an additional attribute is "has been viewed n times."
  2. Edit: additional attributes should appear in alphabetical order before the images.
  3. Navigation
  Selected embodiments may include the notion of an Attribute Group—each attribute may be assigned to one attribute group. User can add multiple attribute groups to a case. The extra attributes for each added attribute group will then be available in the case editor/case view for that case. In the editor, Text area attributes will appear at the bottom of the text tab; others will appear toward the bottom of the properties tab.
Create Attribute:
  After submitting, instead of loading the "edit attribute" form, print "Create another?" and reload the "create attribute" form, blanking out the name field but keeping the other values sticky.
embed multiples as choices in the form field, e.g., for structured vocabularies:
dropdown menu (single choice)
dropdown menu (multiple choices allowed)
radio buttons (single choice)
checkbox list (multiple choices allowed)
  Change the label "Form field" to "Form Element:"
  Omit the phrase "Options determined by Type/Multiples selections".

Add a link in small font "Create new group" to the right of the Group dropdown, which links back to attribute-manager.pl.
Case Editor:
  Instead of having a scroll list & submit button for setting Attribute Groups, use checkboxes, e.g.:
    Additional Attributes:
    [ ] Pathology [ ] Cardiology [ ] Numerology
  Use JavaScript to make the checkboxes behave like form submissions so the user don't need a "Set Attribute Groups" button, e.g., each time the user checks or unchecks a box, behave as if "Set Attribute Groups" was pressed.
  Use a four-column lathe usert for the checkboxes.
  The "Additional Attributes" section does not appear at all if there are no attribute groups.
  Selective embodiments may also include
Ordering Attributes:
  Allow admin to control order of attributes within an attribute group, using sequence numbers.
  Also, allow admin to control order of attribute groups themselves, as they appear in case viewer and case editor.
Special "All Cases" Attribute Group:
  Allow admin to designate that certain attributes should be part of every case. To the end user, these special attributes may appear just like default case attributes, and the fact that they are "custom" may be transparent. To support this, a pre-existing special attribute group called "All Cases" may be used, whose attributes may always be displayed in the case editor. Users may not be able to hide these attributes. Properties belonging to "All Cases" may appear just above the "Additional Attributes" section, without being contained in a group box, and text areas belonging to "All Cases" won't show "(All Cases)" in label. Finally, add the "All Cases" attributes to admin-config-fields.pl, so the admin can specify optional/required/disabled.
  Custom Category Drill-down
  Create a private top-level system folder owned by admin, called "Cases". Admin may be able to populate it with an arbitrary category hierarchy.
Case Editor
  In the Properties tab of the Case Editor, under Anatomy and Pathology, add a new case attribute "Category:" whose dropdown menu contains the contents of the Cases folder. This provides a controlled interface to the private
  Category folder: even though the Cases folder hierarchy is private, the case author may be able to assign the case to a subfolder in the hierarchy using this controlled mechanism.
  Like other case attributes, the Category attribute may be subject to disabling/enabling/requiring.
  The dropdown menu for the Category attribute may be slightly different from adding a case to a folder. First of all, the contents may include the entire Category folder hierarchy, regardless of whether or not the end user has write permission to any of the subfolders. Also, rather than use the "Foo>Bar>Baz" syntax, for each node, display only the name of the current node, indented, as follows:
    Chest:
      Normal Variants:
        Chest wall—soft tissue
        Chest wall—osseous structures
        Diaphragm
      Neoplasms:
        Bronchial carcinoma
        Bronchial carcinoid
      Vascular:
        Foo:
          Baz1
          Baz2

Only leaf nodes may be selectable. Non-leaf nodes may be appended with a colon (:) to give a visual clue that they are different from leaf nodes.

Changing the Category attribute for a case should 1) create a new FolderCase record, and 2) fill in the MedCase.category attribute with the oid of the new FolderCase, 3) if the attribute previously contained a different FolderCase oid, delete the old FolderCase.

Advanced Search

Add a Category constraint underneath Anatomy and Pathology. Unlike the dropdown menu in the case editor, non-leaf nodes may be selectable. A case matches a Category constraint if it is filed at or beneath the selected node.

Administrative Options

Add configuration option called "Configure Case Manager". Currently, it will have only one choice:
Primary Drill-Down:
(*) Use Anatomy>Pathology
( ) Use Custom Categories Case Manager If the drill-down is configured to use custom categories, then under Shared Cases and My Cases, show the top level of the Cases folder instead of the Anatomy categories. For the My Cases drill-down, the case counts should be customized to only show number cases owned by the user.

The Cases drill-down should behave similar to drilling down through any folder, except that the "Top>Folders>Cases" prefix of the breadcrumb should be replaced with "Top>Shared Cases" or "Top>My Cases".

For dropdown menu, allow non-leaf nodes to be selectable. Get rid of the colons. If indenting is viable, use it for all folder dropdowns.

When drilling down, keep track of the context of whether or not the user came from Shared Cases or My Cases, and then hack the Folder code so that in the special case of "My Cases", it filters out cases not owned by the user.

Create a subfolder under Cases called "Unassigned". Put all unassigned cases there. Whenever a case is assigned, be sure to remove it from Unassigned.

If the Cases hierarchy is edited using the Folder Options, be sure to update the Category attributes for all affected cases. This applies whenever a subfolder is moved or deleted, or whenever a case is manually moved or removed. e.g. if a folder is deleted, all cases within the subtree may be added to "Unassigned".

The selector in the editor may be made up of 2 HTML SELECTS
Categories: Subcategories:
Choosing a category may cause subcategories to be populated with the relevant subcategories.
Controlling "when to Display"

Users may be able to incrementally view text by clicking on tabs for each text section. Certain features may be dependent on whether TM is on or off. For example, the title may not be displayed if TM is on. Also, if TM is on, certain thumbnails may not appear until certain text sections are revealed. The author will still be able to control when thumbnails appear through a dropdown menu in the Case Images tab of the case editor, but we are changing the values for that dropdown menu. Use the following prompt:
During Training Mode: [Display Always]
The dropdown menu may default to DISPLAY ALWAYS, with the following additional choices:
Display Always
Hide Until History
Hide Until Findings
Hide Until DDx
Hide Until Diagnosis
Hide Until General Disc.
Hide Until Specific Disc.

Omit any labels which correspond to disabled attributes. If "Specific Disc." is disabled, then change the label of "General Disc." to "Discussion".

"when to display" settings for existing cases may be converted, using the following mappings:
"Always"—>"Display Always"
"Always Except During View as Unknown"—>"Hide Until Findings"
"Only During View as Unknown"—>"Display Always"
"Only During Display Findings & Captions"—>"Hide Until Findings"
"Only During Reveal Full Case"—>"Hide Until Discussion" (general)

The delta may be run prior to use of this new form, so the user don't have to worry about legacy data breaking the user's form. Some of the legacy values do not map well to the new system, but we are going to just bite the bullet on that one.

Constraining Image Display to "Append Only".

Text sections may have an implicit "ordering" in time, from left to right. E.g. "Display Always" has a time-value of T=0, "History" has T=1, and Findings T=2. Images can be hidden to "append only": as the user steps forward in time (clicking on tabs), images with higher figure numbers can be appended to the list of visible images, but they may not be allowed to appear in an arbitrary order.

It is not required that this constraint be enforced.

Dropdown menus may be tied together, so that when the user sets a time value T=X for figure N, the other figures may be adjusted as follows for each figure:

```
if figure number > N
    if selected value < X
        set selected value to be X
if figure number < N
    if selected value > X
        set selected value to be X
```

For newly added images, the dropdown menu choices and default value may be copied from the previous image, e.g., a newly added Image 5 may copy the form element from Image 4. (e.g., whatever the maximum display is for the case, use that stage for new images)

When new images are added, have the case images tab scroll to the next-to-last image. The images in the case images tab may no longer be in reverse order.

If case images are reordered, adjust display stages so that they are appended only.

Display stage form fields are to be removed from the File Upload tab. They can only be edited from the Case Images tab.

Search Abstracts Show Matching Search Terms in Context

For search results, matched search terms may appear in each abstract, boldfaced in the context of surrounding words.

Boldfacing may be used to show the matched text within the abstract. As a prerequisite, all existing boldfacing may be eliminated from the abstract, including the title, anatomy>pathology, and image info. If it is a title match, boldface the matched word within the title.

If it is not a title match, change the line of the abstract which currently shows history and diagnosis to instead show the context of the match, as follows:
Show the name of the matching field (e.g. "Findings:"). Display up to N characters (N=25?) which precede the matched text, and up to N characters which follow the matched text. Only show whole words (if the boundary falls within a word, chop out the word). Use ellipses if there are more than N characters within the field preceding or following the matched text, e.g.:
   Findings: . . . blah blah blab blah<b>test anim</b>blah blah blah blah blab . . .
   If it is an AND match, show the context for each of the terms, e.g.:
   Findings: . . . blah blah blah blah<b>test</b>blah blah blah blah . . . foo foo foo foo<b>anim</b>foo foo foo foo.
   or if the words appear in different fields:
   Findings: . . . blah blah blah<b>test<b>blah blah blah . . .
   Discussion: . . . foo foo foo foo<b>anim</b>foo foo foo foo . . .
Note: if training mode is on, the context may not be shown.
Create Multiple Folders Using Tab-delimited Text Hierarchy
   Make a "Create Multiple Folders" form, which is like the Create Folder form except the "Folder Name" field is a large text area (20 rows) which allows users to enter multiple folders, one per line, tab-delimited. Parent-child relationships defined by indentation, e.g.
Breast
   Juicy
   Perky
Abdomen
   Bulging
   Flat
      Six Pack
      Two Pack
   Underneath the text area, print in small font:
   Note: the user must use<b>tabs</b> for indentation, not spaces.
   The user may enter text directly, or cut and paste from a document.
   Use JavaScript to enable tabs.
   As with the single folder creation form, the Location field may specify where the folders are created. It will apply to the top level folders specified in the text area.
   The Description and Permissions fields will apply to all folders (i.e. the user can create a single permission entry to propagate to all folders in the hierarchy).
Allow Users and Cases to be Grouped by Location
   This feature may be designed to be toggleable on customer installations from the admin page.
   If "multiple locations" is enabled, may allow admin to specify a set of locations (similar to Institution on MyPACS.net). Each Location may consist of a text label, but not necessarily a state & country.
   Users may be prompted to select their location from a drop-down menu when signing up or editing their member info (similar to Institution in mypacs.net).
   Case abstracts and views should include location as part of author info (similar to Institution in mypacs.net)
   Allow cases to be filtered by location. For basic search, add radio button "My Location" between "My Cases" and "All Cases"; may add location filter to Advanced Search as well.
   Searching should be efficient for filtering cases by location. Consequently, it may be necessary to add an Object Metadata field Location which propagates to all objects owned by a user at a given location.
Rating Cases
   Support may be provided for rating of cases. For example, a link in case title bar may be displayed that says "Rate".
   Clicking the link may display rating criteria near the top of the case, each with one to five stars. Examples of rating criteria are:

Level of Interest (1 star=ho-hum, 5 star=very cool)
   Text quality
   Image quality
   Usefulness for Board Exams
   The rating interface may include a star system, where the rating is sent to the server without requiring the user to click submit, and criteria which have been rated may show up as yellow stars. Once a user turns on the rating form for a case, "rating mode" may be sticky for the rest of the session, with the rating form appearing at the top of every case. The rating form may have a "hide" link which will turn off rating mode. User can toggle rating mode back on by clicking "Rate" in the title bar of any case.
   Ratings may be shown in the abstract view. To avoid information overload because of the multiple criteria, an "Overall Rating" may be displayed, which represents the composite average rating of all accumulated votes for the case. Show the overall rating in the case abstract, along with the number of votes, e.g.: (*, 3 votes). Average ratings may be shown using red stars, including fractions of stars. If a user has rated a case, their composite average rating for that case may appear as well, using yellow stars, e.g.: (*, 3 votes, the user gave it**).
   In the full case view, show all rating criteria (including composite average) under "additional details".
   Add the various rating criteria to "Sort By". Include each criteria separately, as well as "Overall Rating", which will be the composite average.
   Add rating filter to advanced search:
   Rated At Least: [1-5 star] in [criteria type]
      with a minimum of [textbox] votes.
   Criteria-type should be a popup of all criteria, including "Overall Rating". Cases which have been rated by less than N users may not be considered hits.
   Rating criteria may be editable and extensible by admin. Have a form called "Manage Rating System", which may allow the admin to globally enable or disable ratings in general, as well as to enable or disable each criteria independently, to edit the label for a rating criteria, and to add new rating criteria.
   Assigning stars to multiple variables might be too tedious. Furthermore, some users may be discouraged from submitting cases if they receive low ratings.
   In alternate embodiments, the "rating" system may be removed in favor of a non-quantitative multivariable "recommendation" system. E.g.:
   Recommend this case:
      [ ] Good for Board Exams [ ] Unusual/Challenging
      [ ] Excellent Images [ ] Good Discussion
   Then users may be able to filter search results based on number of recommendations in the variables they care about.
   Add a comment box next to the rating interface, so users can explain their rating with a "review". this type of comment is different than the general discussion comment currently offered.
User Manager Role
   The system may have a special "user manager" role (group) whose membership is controlled by the admin. User Managers may have a subset of admin privileges. For example, they can:
   Modify a user's password
   Modify a user's account information
   Suspend a user's account
   Restore a user's account
   Limit private cases
   Reassign cases Demotion of Zero-Image Cases For searches: zero-image cases may be demoted to the end of the list when sorting by relevance. However, they may not be demoted when re-sorting by date, title, etc. The current behavior may be interpreted as a bug by most users who try to resort their search results.

For folders: zero-image cases may never be demoted. They may be demoted when resorting by title, etc.

For category drill-down: zero-image cases may be demoted in the default view. An additional sort choice may provide for a category drill-down wherein zero-image cases are not demoted, such as if resorting by date.

Windows/Levels: Controls for Relative Adjustment

Directly under the W: and L: textboxes, add image buttons "−contrast+" and "−brightness+" as follows:

W: [223] L: [445]

−contrast+ −brightness+

Apply to: (*) This slice only ( ) Entire Series

Clicking on "−" for contrast should have the following automatic effect:

if "Apply to" is on "Entire Series", switch to "this slice only"

compute new window value=120% of its current value show the new numeric value in the W: textbox submit the "Adjust W/L" button Clicking on the "+" next to contrast should have the same effect, except it should REDUCE window to be 80% of its current value.

For brightness, the direction is reversed: "−" should reduce level to 80% and "+" should increase level to 120%.

Change Tracking & Version Control

Basic version control may be provided for cases. Every time case text, properties, or captions are edited, a historical record of previous version of the case record (and caption record) may be updated.

Under "Additional Details", provide a link "revision history" (for owner or admin) which shows a list of all revisions ordered by date. Each revision may list fields that have changed, including the old value and the new value. Next to each revision, provide a link "revert to this version" which rolls back the changes to that point.

Structured Diagnoses

Diagnoses can adhere to a structured keyword list. A keyword may be a key phrase (can contain spaces). An author can select from dropdown menu or enter a free-text value.

In addition to structured searching and automatic cross-referencing of related cases, an automatic quiz-mode may be provided in which the user can try to guess the diagnosis (this will be especially powerful when combined with a differential database that automatically suggests a list of alternative diagnoses).

The keyword database may start with a list of all diagnoses from an authoritative source. The dropdown menu may be filtered by anatomy/pathology choices to only show relevant diagnoses.

The system may allow any number of diagnoses per case, not just one.

Multiple DICOM Queues

Provide admin interface for creating new queues with their own AE_TITLE, and controlling access to these queues using group membership. Images sent to one queue may not be accessible from any other queues. Only members of the group associated with a queue may be able to browse that queue when assigning images to cases. Users may be able to select which queue they want to search from the DICOM tab.

add new admin option: manage DICOM queues

Manage DICOM Queues create new queue named: [textfield for name] [Submit]

<queue1>

<queue2>

<queue3>

... list all dicom queues (hyperlink to each queue management page, labeled by AE_TITLE)

Clicking "Submit" to create a new queue may create the new queue using all default settings, with a hyperlink to the queue added to the list, so the user can just click the link to go to the queue management page and customize it.

Each queue management page may look like this:

breadcrumb: Manage DICOM Queues>$ae_title

Disk space used: [show disk space used by this queue]

Total available:

<delete selected dicom studies> (hyperlink to Delete page)

Allow this queue to be accessed by: [dropdown menu of all groups]

Default choice: All Users

"Delete Selected DICOM Series" may be a forest of all DICOM queues. Specify disk space used for each queue separately. An optional URL parameter may be provided to specify the AE_TITLE of a particular queue, so the user does not have to populate the whole forest if the user is navigating here from the "Manage DICOM Queue" page.

For DICOM tab of case editor, for each DICOM queue group that a user is a member of, include a checkbox with the ae_title allowing them to control which queues to search over. Default to all checked.

Enhance automatic purger to handle multiple queues. In some embodiments, there may be a single purge policy for all queues.

Add a section at the top of the page (above the Disk Usage section):

DICOM QUEUES:

AE TITLE PORT ACCESS DELETE title 1 2222 [dropdown set to: ALL USERS] [ ]

title 2 3333 [dropdown set to: TUMOR BOARD] [ ]

[[SAVE CHANGES]]

Add Another Queue:

AE TITLE: [ ] Port: [ ] Access: [dropdown] [[ADD]]

Clicking [[ADD]] reloads the page with the new queue appearing in the table.

In the table, the titles and ports can be text fields, which is a convenient way for the admin to edit these values.

The "delete" checkbox may be used to remove a queue. If the admin tries to delete a queue that is not empty, print a message "The user may not delete the queue unless the user empties it first." A queue may be considered "empty" if it was cleared out using the "Manually remove selected studies", even if there are some undeleted images in cases that originated from the queue. Deleting the queue may not affect these images.

Change the name of the space reclaim page back to "Manage DICOM Queues", and change the label of the link on the options page.

DICOM Search Pane

Preload the form with the most recent N patients, opened to the first page, so if the user's exam was recently pushed it may be visible immediately. If the search form is submitted with all empty values in the "match on" fields, treat it like "get everything".

Folder Search
ability to constrain search to a folder.
in advanced search, constraint:
Look in Folder: [popup menu of folder choices, default ANY] search should include subfolders.
This should also be accessible from folder options page: "Search for Cases Under this Folder".
Lock as Unknown
Give case authors the option of locking their case in unknown mode, which will support quizzes (user can unlock it after the quiz date is over). Add a checkbox in case editor "lock case in unknown mode".
Keep Track of Visited Cases
Keep track of every case a user visits. Have an open book icon appear in case abstracts next to those which have already been visited. Provide a "mark as unread" option at the case view level. Provide a user option to "mark all cases as unread".
Additional Info to Explain Some of the Features in One Embodiment
Category Drill-Down
The system enables users to access cases by drilling down through anatomy and pathology categories. At each level of the hierarchy, all sub-levels are displayed as links, with a magnitude indicator showing how many combined cases are available at that sublevel. Magnitudes may be computed on the fly using a database query, or cached. If cached, the cached values may be updated whenever a case is created or an existing case is reassigned to a new category or folder. In response to clicking a sublevel while browsing categories, each user may be presented a listing of cases which are accessible to that user, but not cases which are inaccessible (e.g., due to access control settings). This may include cases the user owns, cases that are public, and cases that are viewable by a group the user belong to. Cases which are private or shared with groups that the user does not belong to may be hidden from view.

The user may drill down to cases by Anatomy and Pathology categories.

To the right of each category is a number in parentheses, specifying the total number of accessible cases under that category. The "Other" category lists cases which do not match any of the predefined categories. The "All" category lists all cases by pathology, regardless of anatomy. If there are no accessible cases under a particular category, that category is omitted from the list.

The user may click on one of the Anatomy categories to see a list of Pathology Categories under that anatomy.

To the right of each pathology subcategory is a number in parentheses, specifying the total number of accessible cases under that category. The "All" category lists all cases matching the anatomy, regardless of pathology. If there are no cases under a particular category, that category is omitted from the list.

The user may then click on one of the Pathology subcategories to see a list of cases matching both the anatomy and pathology.

For each case in the result list, an abstract may be displayed showing the title, case number, patient demographics, number and modality of images, history, diagnosis, author, and date created or last edited. Some of these fields may be hidden if the user is in Training Mode.

By default, cases may be ordered by date. Newest and most recently edited cases appear first. The user can reorder search results using the "Sort By" drop-down menu that appears to the right of the results list. The user can order results by title, case number, author, or certification status. If the user is logged in, an open book icon means that the user has previously visited the case, whereas a closed book icon means that the user has never visited the case before. The user can reset the user's visitation stats from the Options menu.

A visual indicator (e.g., a green checkmark) next to a case title may indicate that the case has been Certified.

The search results may only include cases which are accessible by the user. Cases which are private or shared with groups that the user does not belong to may not be returned.

The user may then click on one of the cases abstracts to see the full case view.

A breadcrumb trail above the case title may show the full path to the case. Clicking on any of the links in the breadcrumb trail will take the user back to the category listing. Clicking on the Prev and Next links may cycle through the cases in the list.

The case view displays all fields associated with the case, including author, patient history, images and captions, findings, diagnosis, discussion, and references. If there is no text for a particular field, that field may be omitted from the case view. The user can also see comments left by users who have visited the case. The Additional Details section at the bottom of the case includes the case number, date that the case was last updated, anatomy and pathology categories, modalities, exam date, access level, keywords, and number of times the case has been viewed.

Basic Search may allow the user to perform a full text query on any of the text fields in the case, including the case number, title, keywords, history, findings, diagnosis, discussion, references, image captions, and comments. To limit a user's search to only specific fields, or to filter cases on properties such as modality, author, age, gender, or exam date, see the section on Advanced Search. To perform a basic search, the user may enter a case number or search terms in a text box. The system may return the case matching the case number, or a list of all cases matching the search terms or that was entered. Cases which contain the search string embedded in a larger word are also returned. For example, "endo" will match cases containing "endometrial," "endosteal," and even "tendons." To limit the user's results to cases matching an exact phrase, surround the user's search terms in quotes. For example, "left lung" with quotes will not match a case containing the text masses in the left and right lung, whereas left lung without quotes will match the case, even though the words are not immediately adjacent. If the user is logged in, choose whether to search in All Cases or My Cases. Choosing "My Cases" will constrain the search to only those cases which the user own. The default is "All Cases".

The Advanced Search form may allow the user to construct a query over any combination of attributes. The Advanced Search Form may contain a large number of parameters that allow the user to constrain the search by various case attributes. If a parameter does not appear in the user's search form, it is because that attribute has been disabled by the administrator. All parameters are optional, and if the user leaves a specific parameter in its default setting, it will not affect the user's search. The search engine may perform a Logical AND over the user criteria, search, meaning that a candidate case must match ALL specific criteria or it will not be included in the search results.

Example elements are:
Text match—Enter a word or phrase to look for.
Match on—If performing a text match, use the checkboxes to select which case elements to include in the search. Uncheck those boxes which the user does not want to match. This gives the user more control than the Basic Search. For example, if the user wants cases whose diagnosis is pneumonia but not cases which happen to mention pneumonia somewhere in the text, enter pneumonia in the text match box and uncheck all the checkboxes except 'Diagnosis'. Use the "Select all" checkbox as a shortcut for selecting or detecting all the elements at once.

Owned by—Enter the login ID of a user to constrain the user's search to cases owned by that user's account. Note: if the user is looking for cases authored by a specific user, the user should leave this field blank and use the "Authored by" field instead. If the user does not know the user's login ID, the user can use the "Find User" link to look up the user by name (in a different window), then enter the login ID here.

Authored by—Enter the login ID of a user to constrain the user's search to cases by a specific author. If the user doesn't know the user's login ID, the user can use the "Find User" link to look up the user by name.

Last Updated—To find cases which were created or updated on a specific date, choose 'ON' in the first drop-down list, and specify a day, month, and year. The user may also find older cases using BEFORE and newer cases using AFTER.

Anatomy—To constrain the search to a specific anatomy, select a category from the drop-down list. These categories correspond to the top-level categories in the Case Manager.

Pathology—To constrain by pathology, select a category from the drop-down list. If the user specifies a Pathology without an Anatomy, the user can find cases matching that pathology regardless of anatomy.

ACR Code(s)—If the user's institution uses American College of Radiology (ACR) codes, the user can enter them here. These may not be widely used, and the user might get more hits by using the Anatomy and Pathology drop-down menus.

Modalities—Click one or more checkboxes to constrain the search to cases containing specific modalities. If the user specifies more than one modality, the search results will include cases containing any of the selected modalities. For example, if the user clicks "MR" and "CT", the user will get cases containing either an MR image, a CT image, or both.

Patient Information—The user may constrain the search to patients in a specific age range or gender. If the user's system is configured to allow patient names and medical record numbers, the user can enter those attributes to look up cases associated with a specific patient. This feature may be disabled by the user's administrator.

Exam Date—This field allows the user to search for cases based on the date of the exam (if it was entered by the case author). To find cases whose exam occurred on a specific date, choose 'ON' in the first drop-down list, and specify a day, month, and year. The user may also find cases whose exam occurred BEFORE or AFTER the specified date.

Certification Status—To find only cases that have been approved by an authority, select 'Certified' from the drop-down menu. To find only uncertified cases, select 'Uncertified'. For more information, see Certifying Cases.

Private or Shared—Search in "All Cases" or "My Cases"

If the user is logged in, choose whether to search in All Cases or My Cases. Choosing "My Cases" will constrain the search to only those cases which the user owns. The default is "All Cases".

Training Mode allows the user to view cases as unknowns, and sequentially reveal case text in stages, for example:

1. View as Unknown—Patient demographics and history are displayed, but the case title and other fields are withheld. Images are displayed with no captions. The user can study the images and try to identify the findings.

2. Reveal Findings & Captions—The use can read the findings text and try to predict the diagnosis. If the case contains annotated images showing the findings, they will appear as well. This stage is skipped if the case contains no captions or findings text.

3. Reveal Full Case—The entire case is displayed, revealing the diagnosis and discussion.

Training Mode is useful for self testing, as well as for conferences, allowing the presenter to control the information displayed to the audience.

To turn training mode on, use the control on the right side of the screen above the navigation bar:

With training mode is on, whenever the user performs a search or drill down to a list of cases, the case titles may be replaced by case numbers, allowing them to be explored as unknowns:

When the user navigates to a case with training mode on, it is first displayed in Unknown mode. The training stage controller appears above the case, allowing the user to traverse to the next stage.

If the case has findings and/or captions, the user can click on "Reveal Findings & Captions" to view them. Captions may appear beneath each image, and Findings text may appear at the bottom of the case. If the author included annotated images showing the findings, they may also appear at this stage.

Click on "Reveal Full Case" in the training stage controller above the case to see the title, diagnosis, and discussion.

If there are more cases, the user can visit the next case by clicking on "Next" to the right of the breadcrumb trail, and the next case will appear in Unknown mode. Training mode will stay on until the user click "Turn Off" in the controller above the navigation bar.

Posting Comments

The user can post comments to any case. Comments can be either public (viewed by anyone) or private (viewable by only the comment author). Comments are useful for leaving searchable notes about a case, leaving feedback for the case author, starting a general discussion, pointing out additional findings, or questioning the validity of the case. Depending on how the system is configured, the owner of a case may receive an email every time a comment is posted to his case.

In an example embodiment, to post a comment:

1. Be sure that the user is logged in and Training Mode is turned off.

2. Click on "post a comment" which appears near the end of the case, above "Additional Details":

3. The comment form appears, allowing the user to enter text and select Public or Private. If the user chooses Public, all users visiting the case will see the comment.

4. Click "Submit Comment". The comment is now attached to the case.

Method for Presenting Cases at Conferences or Rounds

Institutions often have weekly conferences where residents and staff meet to go over educational cases. Rather than creating PowerPoint presentations, the user may present cases directly from the teaching file system. By using the teaching file manager to host the conferences, the user avoids incurring the overhead of creating PowerPoint presentations, and the user may have a historical record of all case presentations.

1. Have the administrator create a top level folder called "Conferences".

2. Under the Conferences folder, create a subfolder for each conference date.

3. During the week, whenever someone encounters an interesting case, they can copy it into the folder for presentation at the weekly meeting.

4. When the conference begins, project the teaching file system directly on the display screen, turn on Training Mode, and navigate to the conference folder.

5. If the user's cases contain patient identifiers, the user may want to keep them hidden for the conference. They are hidden by default. The user can toggle identifiers by clicking "hide/show identifier" to the right of the patient information.

6. During the meeting, each participant can come forward in turn and click on their case. With training mode on, the presenter can discuss the case as an unknown and quiz the audience on the findings.

7. The presenter may use Full Screen mode for optimal presentation of images.

If a user's PACS workstation or modality is configured to send studies to the teaching file server, then the user can avoid having to export files and upload them as separate steps. Once a study is in the teaching file's DICOM queue, the user can access the study from within the Enhanced Case Editor, browse the stack of images, adjust window/levels, and add selected images to the case.

Because of the asynchronous nature of the case editor, the user does not have to wait for some parts of the application to finish loading before doing work in other parts. For example, while waiting for the DICOM tab to finish loading, a user can enter some case properties (such as a title). When the "DICOM" lettering turns black, the user will be able to click on it to access the DICOM tab.

A user can search by first name, last name, patient number, or accession number. The user doesn't need to enter the entire search string—a user can search by prefix. For example, "Jo" in the last name field will match "Jones" and "Johnson". Note that a user may not be able to query the PACS directly—the user must first push a study to the teaching file's DICOM queue before the user can access it here.

The DICOM interface may automatically show patients in the queue. Results may be listed by patient in the order they were received in the queue (most recent appearing first). Under each patient is a list of exams, showing the accession number, exam description, and exam date. Under each exam is a list of series, showing series number, size, and the date and time the series was pushed to the teaching file server:

The DICOM viewer may support the following operations:

Scroll up and down through the image stack: position the mouse over the image and use the user's scroll wheel. A user can also click prev/next or drag the slider control.

Adjust the window/level: enter new numeric window/level values in the text boxes and press "Adjust W/L". To increase contrast, enter a narrower window value. To increase brightness, enter a higher level value. Use the radio buttons to specify whether to apply the new W/L to the current slice or the entire series. If the series is large, it may take several seconds for the entire series to be adjusted. A user can also use the presets in the dropdown menu if any are available (currently, only CT presets are supported). A user can return to the original W/L settings using the "Image Defaults" preset.

Add an image to a case: scroll to the image the user want to add, adjust the W/L if desired, then press "Add to Case". The Editor may immediately switch to the Case Images tab. After a few seconds, the new image will appear in the tab above any existing images. A user can then enter a caption. See Managing Case Images for more options. If the user wants to add additional images, click on the DICOM tab and repeat the process.

When an image is first added to the case, the DICOM header information is automatically imported into case properties. For subsequent images, if there are any conflicts in DICOM properties from the currently populated values, a popup window appears which shows values extracted from the DICOM header, including patient name, patient number, sex, age, study date, and modality. The right column shows the current value of the properties in the case, if they exist. If a user wants to avoid overwriting any existing case properties, uncheck those fields the user want to keep unchanged. When the resolver is submitted, the editor may switch to the Case Properties tab, with the new property values filled in where appropriate.

Once a user has added images to the case using the upload method or the DICOM method, a user can edit image captions, reorder images in the case, delete images, and control when each image is displayed during training mode. For each image, a user may edit the following properties:

Caption: enter a new caption, or edit the existing caption. Caption text is indexed by the search engine just like other case text fields. The user can choose to enter a paragraph of image findings here, or limit captions to descriptive labels (e.g. "Axial T2"). Captions will not be displayed when the case is being viewed in Unknown Mode, so it is safe to describe findings here if the user choose to do so. The user does not need to enter figure numbers, as they will be automatically generated when the user save the case.

Display: control when an image is displayed. The default value is Always, which means that the image will appear regardless of what stage of training mode the user is in. Other choices are to hide until various stages of the case are revealed (e.g. Findings, Diagnosis, Discussion).

Order: enter a different sequence number to change the order of an image. A user may enter a fractional number to move an image between two other images. For example, a user can enter "2.5" to have the image appear between current images 2 and 3. The system will automatically adjust the figure numbers to accommodate the new ordering.

Delete: click the checkbox to remove an image from the case. When a user submits the form, the image will be irrevocably deleted from the repository.

Certifying a Case

Cases can be certified by qualified personnel to confirm their accuracy and quality. In search results, certified cases may appear before non-certified cases, and they are marked with a visual icon (e.g. a green checkmark). The identity of the person who certified the case appears in the case. Depending on an institution's teaching file certification policy, the administrator may be able to grant the user Certifier privileges. If a user has been assigned the role of Certifier, the user will see a "Certify" link on the right side of the title bar of every non-certified case. After reviewing the case to determine its accuracy and quality, if a user decides to certify the case, simply click the Certify link and then confirm the user's intent to certify the case by clicking CERTIFY. The case will now appear as certified to all users who view it. If the case is ever edited, the certification status may reset to uncertified. If a certified case is edited, it may lose its certification status. Depending on the policy configured by the system administrator, ownership of certified cases may be automatically transferred away from the author to preserve certification status.

Shared Folders

Users may store references to cases in hierarchical folders, and share these folders with other users using the group-level access control. Each user may have an individual home folder. There may also be a top level folder controlled by the administrator. Folders may have user-assignable names and text descriptions, which can be searched on. If a user keeps the folder Readable By "Owner Only", then nobody else will be able to view the folder (if they visit the parent folder, they will see a message explaining that there is a "hidden" subfolder). If a user makes a folder Readable By "All Users" (or a group), then other users may be able to view the contents of the folder. Note: if a user chooses to share the folder, it is located in a folder which is accessible by its intended users. For example, if a user makes the folder readable by "All Users", but it resides in a folder that is readable by "Owner Only", no one will be able to access it. If a user keeps the folder Writable By "Owner Only", then nobody else will be able to alter the contents of the folder. If a user makes a folder Writable By other users, they may be able to perform the following actions:

Add and remove cases from the folder
Add subfolders to the folder
Remove subfolders that they have added to the folder
However, they may not be allowed to perform any of these operations:
Delete the folder or move it to a different location
Rename the folder or edit its description
Change the folder's permission settings
Reorder the folder contents
Only the owner or the administrator may be able to perform those privileged operations.

When sharing folders, a user may share with all users, or members of a group. The dropdown menu may display all groups that the user is a member of. See Managing Groups for more information on creating and participating in groups.

A user may add cases to any folder that is writable by the user's account. This includes folders the user has created, publicly writable folders, and folders that are writable by groups the user belongs to.

Removing a case from a folder or deleting the folder may have no effect on the case itself. A particular case may be referenced from any number of folders.

When a user adds cases to a folder that is owned by another user, the folder's owner may remove the user's cases if he or she wants to.

A user may add multiple cases at a time to a folder whenever a user is viewing a list of cases, including:
  search results
  a list of cases by category (e.g. "Lung>Neoplasm")
  the contents of another folder Once the reference to a case is added to a folder the Additional Details section of the case view will provide links to all the folders the case is referenced in.

When changing properties of a folder, if the folder contains cases and/or subfolders, specify whether the new permissions should apply to this folder only (default), or to the contents of the folder. If a user chooses to apply the changes to subfolders, it may recursively change the permissions of all folders owned by the user which reside underneath this folder. Subfolders owned by other users will not be affected (unless the user is an administrator). If a user applies the changes to cases as well, the permissions of all the cases that a user owns which are referenced by any of the subfolders may be recursively changed. Other user's cases will not be affected.

Groups

End-users may create a new group. From the Create New Group form, enter a name for the new group, and click the checkboxes next to the users who the user wants to add to the group. A user can now share cases and share folders with the new group.

Publishing Cases to a Public Teaching File Server

Publishing allows a user to send copies of the user's cases to other teaching file servers that reside outside the hospital firewall so they can be viewed by the public. When a user publishes a case, patient identifiers may be withheld from the case fields (although a user still need to be careful not to publish screen shots containing patient identifiers). The system may be configured to allow publishing to one or more destinations, including possibly a publicly accessible teaching file server managed by the user's institution. To determine whether or not a user account is enabled for publication, visit one of the user's cases and look for the "Publish" link in the case title bar. If it does not appear, it means that a user does not have publication privileges, in which case the user may contact the administrator for help publishing. A user may publish a case if (1) a user has write permissions on that case and (2) a user's account has been granted publication privileges. To publish a case visit the case a user wants to publish, and click the "Publish" link in the case title bar. From the publication form, a user may be prompted to select from a menu of possible destinations. If a user does not see a destination menu, it means that there is only one possible destination. Enter the login credentials of an account on the destination server, and submit. The published cases are available on the destination server. They may be owned by the account which the user specified in the publication form.

To publish multiple cases at once, add them to a folder, and then publish the contents of the folder, using an interface similar to that described for publishing a single case.

Exporting Cases as HTML for Viewing Offline

A user can export cases as standalone HTML, which the user can save to a disk for accessing when the user is not connected to the intranet. For example, a user can use this to save cases for presenting at a conference, or to study at home. A user may only export cases which are writable by the user's account. Exported cases may be packaged in a container, such as a Zip file, which enables a user to download multiple files in a single operation. Once published, click on the case link to view a user's offline copy of the exported case. To export multiple cases at once, add them to a folder, and then export the contents of the folder. This may export all cases in the folder that are writable by the user's account. If the folder contains cases which are not writable by the user, they will be skipped. The published cases are contained in a zip file. The zip file contains an HTML index page with links to all the published cases.

Special Privileges

Certification—this feature may allow an administrator to designate users as certifiers (reviewers). Users who have become certifiers may see a "Certify" link in the title bar of cases that they view. Certifiers can click the option to designate that the case meets the institution's quality standards. The case may be marked with a green checkmark to indicate that it has been certified (and the name of the certifier will appear at the bottom of the case). If a certified case is subsequently edited, it loses its certified status and must be recertified. To grant certification privileges to users, the admin selects the checkbox next to each user. Deselect a checkbox to remove certification privileges. To make the certification workflow more useful the administrator can automatically set up a change of ownership once a case is certified. Ownership can be transferred to the user who is actually certifying the case, or ownership can be transferred to a designated user. To set the change of ownership status select one of the radio buttons and click the Update Policy button. Enter the user login ID in the free text field to designate a specific user. The current owner of the case will get an email announcing the case has been certified and ownership has been transferred.

Publication—this feature may allow the administrator to control which users are able to publish cases outside the user's institution to the World Wide Web. There are three policy options:

Disable Publication

Enable All Users to Publish

Allow Members of Publishers group to publish

If the administrator selected the third option, then the administrator can control which users are able to publish by checking the box next to the user's name and clicking UPDATE MEMBERSHIP.

An administrator can use the "Grant Special Privileges: Authors" option to transfer authorship privileges between accounts. For example, if some residents rotate out of the department, the user can transfer their privileges to new residents. Accounts which lose authorship do not lose their cases or login ability, they just lose the ability to create or edit cases.

To remove author privileges from one account and assign it to another, simply uncheck the checkbox next to the account losing authorship, and check the checkbox next to the account that an administrator wants to have authoring privileges. Click UPDATE MEMBERSHIP to save the user's changes. The administrator will not be able to save changes if the number of checked accounts exceeds the author limit.

System Commands:
  Reclaim Space from the DICOM Queue—The administrator can manually clear out unused studies from the queue or have the system automatically purge. To automatically set purging, under "Automatic Purging", enter the number of days a study shall remain in the queue before it gets deleted. If a study has an image being used in a teaching file case then the system will not delete any of the images from that study. Automatic purging only deletes studies where none of the images are being used in a teaching file case. The automatic purge can also be turned off.

Under "Manual Purging", the administrator can manually purge unused studies by setting the number of days a study has been in the queue and then clicking PERFORM PURGE NOW. Like for automatic purging, if a study has an image being used in a teaching file case then the system will not delete any of the images from that study. Manual purging may only delete studies where none of the images are being used in a teaching file case.

The administrator can also manually delete studies under "Manually Delete Selected Series". Use the tree menu to select the study to delete, and then click DELETE SELECTED SERIES. When the user manually delete a study all images not contained in a teaching file case will be removed. This is different from purging where all images from a used study remain.

Configure Case Fields—this feature may give the user fine-grained control over each of the fields associated with a case. To configure case fields select from the drop down menus next to the field names and click SUBMIT when finished. For each field, the user can choose one of the following settings:
  Optional—Field appears in case edit form and advanced search form. Case authors may choose to leave it blank.
  Required Field appears in the case edit form and advanced search form. Case authors must supply a value. Submitting a case with a required field left blank will result in an error message to the case author. Case Edit form identifies required fields with a red asterisk.
  Disabled Field does not appear in case edit form or advanced search form. Field is omitted from case views (even if the field is already populated for existing cases).
  Export All Cases—Clicking this option may cause a zip file containing all cases in the repository to be created. The zip file may contain static html versions of the cases in MyPACS.
  View Schemas—Provides a view of the database tables that are used by MyPACS to model the user's data.
  View Stored Deleted Cases—This option will only show up if the option to store deleted cases for review is checked under Other Configuration Settings (see below). If the option is turned on, deleted cases are added to a queue which the administrator can review by clicking on this option. To reclaim space, the user can use the checkbox control to irrevocably purge deleted cases from the system. To undelete a case, click on the case and click Restore in the case title bar.
  System Information—Provides information about the current version, including:
  Version number and License information
  Number of Cases, Images, and Users in the Repository
  Author limit and number of author slots currently assigned.
  Accounts which have Administrator privileges
  All user sessions that have been logged for the current day
  Other Configuration Settings—This form allows the user to control several local configuration settings, including:
  Set the local contact email, which will appear in several places such as the Account Registration page.
  Activate the signup alert emailer, which sends an email to the local contact address whenever a new user signs up.
  Set the validation password, which users must enter to sign up for a new account. By unchecking the require box, users can sign up without using the password.
  Suppress display of source institution for cases published to this installation. If the user open the user's system for receiving published cases, checking this box will cause the source institution to be hidden (this is useful if all the user's published cases are coming from a single institution).
  Store deleted cases for administrative review. Checking this option may cause cases to be saved in a special queue when they are deleted. The administrator can undelete or purge cases using the View Stored Deleted Cases system command (see above).
  Automatically grant author privileges to new users if under the author limit. This may allow all new users to begin creating cases immediately. Uncheck this box to require the admin to assign authorship privileges to new users.

As such, then, some embodiments of the invention may provide several advantages to a user of a computing device seeking to view and manipulate medical data, such as medical images and medical case files. Embodiments of the invention may provide users with medical images of an enhanced resolution such that users may zoom in on and otherwise manipulate images while limiting problems with pixelization and distortion of images. Some embodiments of the invention may provide users with the ability to generate medical case files from an electronic message.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method comprising:
   receiving a request for an image from a client device, the request for an image being indicative of a requested image;
   retrieving a source image corresponding to the requested image from a memory;
   processing the source image to generate a second image having a greater resolution than the source image;
   providing the second image to the client device to facilitate viewing and manipulation of the second image at the client device;
   receiving a request from the client device for images related to the requested image;
   searching a plurality of images stored in memory to determine one or more images related to the requested image based at least in part upon a diagnostic criteria associated with the requested image; and
   providing the determined one or more related images to the client device to facilitate viewing and manipulation of the determined one or more related images at the client device, wherein the requested image is a medical image.

2. A method according to claim 1, wherein processing the source image comprises processing the source image at a data server.

3. A method according to claim 1, further comprising:
   determining a display resolution associated with the client device; and
   wherein processing the source image comprises processing the source image to generate a second image having a greater resolution than the source image based at least in part upon the determined display resolution.

4. A method according to claim 1, further comprising:
   receiving an indication from the client device of user manipulation of a property of the second image beyond a threshold value;
   processing the source image to generate a third image having a greater resolution than the second image; and
   providing the third image to the client device to facilitate viewing and manipulation of the third image at the client device.

5. A method according to claim 1, wherein the requested image is a member of a series of images; and further comprising:
   retrieving additional images in the series of images from memory; and
   providing the additional images in the series of images to the client device to facilitate viewing and manipulation of the series of images at the client device.

6. A method according to claim 1, wherein the source image is a medical image formatted in accordance with the Digital Imaging and Communications in Medicine standard data format; and
   wherein processing the source image comprises processing the source image to generate a second image having a greater resolution than the source image, wherein the second image is formatted such that it is viewable in a general purpose viewing agent.

7. A method according to claim 1, wherein the source image is a medical image formatted in accordance with Digital Imaging and Communications in Medicine standard data format; and
   wherein processing the source image comprises processing the source image to generate a second image formatted in accordance with a second image format, the second image format being different from Digital Imaging and Communications in Medicine standard data format.

8. A method according to claim 7, wherein the second image format comprises an image format compatible with viewing in a web browser.

9. A method according to claim 8, wherein the second image format comprises a Joint Photographic Experts Group format.

10. A method according to claim 8, wherein providing the second image to the client device to facilitate viewing and manipulation of the second image at the client device comprises providing the second image to the client device to facilitate viewing and manipulation of the second image in a web browser implemented on the client device.

11. A computer program product comprising at least one non-transitory computer-readable storage medium having computer-readable program instructions stored therein, the computer-readable program instructions comprising:
    a program instruction for receiving a request for an image from a client device, the request for an image being indicative of a requested image;
    a program instruction for retrieving a source image corresponding to the requested image from a memory;
    a program instruction for processing the source image to generate a second image having a greater resolution than the source image;
    a program instruction for providing the second image to the client device to facilitate viewing and manipulation of the second image at the client device;
    a program instruction for receiving a request from the client device for images related to the requested image;
    a program instruction for searching a plurality of images stored in memory to determine one or more images related to the requested image based at least in part upon a diagnostic criteria associated with the requested image; and
    a program instruction for providing the determined one or more related images to the client device to facilitate viewing and manipulation of the determined one or more related images at the client device, wherein the requested image is a medical image.

12. A computer program product according to claim 11, wherein the program instruction for processing the source image comprises instructions for processing the source image at a data server.

13. A computer program product according to claim 11, further comprising:
    a program instruction for determining a display resolution associated with the client device; and
    wherein the program instruction for processing the source image comprises instructions for processing the source image to generate a second image having a greater resolution than the source image based at least in part upon the determined display resolution.

14. A computer program product according to claim 11, further comprising:

a program instruction for receiving an indication from the client device of user manipulation of a property of the second image beyond a threshold value;

a program instruction for processing the source image to generate a third image having a greater resolution than the second image; and a program instruction for providing the third image to the client device to facilitate viewing and manipulation of the third image at the client device.

15. A computer program product according to claim 11, wherein the requested image is a member of a series of images; and further comprising:

a program instruction for retrieving additional images in the series of images from memory; and a program instruction for providing the additional images in the series of images to the client device to facilitate viewing and manipulation of the series of images at the client device.

16. A computer program product according to claim 11, wherein the source image is a medical image formatted in accordance with the Digital Imaging and Communications in Medicine standard data format; and wherein the program instruction for processing the source image comprises instructions for processing the source image to generate a second image having a greater resolution than the source image, wherein the second image is formatted such that it is viewable in a general purpose viewing agent.

17. An apparatus comprising a processor configured to:

receive a request for an image from a client device, the request for an image being indicative of a requested image;

retrieve a source image corresponding to the requested image from a memory;

process the source image to generate a second image having a greater resolution than the source image;

provide the second image to the client device to facilitate viewing and manipulation of the second image at the client device;

receive a request from the client device for images related to the requested image;

search a plurality of images stored in memory to determine one or more images related to the requested image based at least in part upon a diagnostic criteria associated with the requested image; and provide the determined one or more related images to the client device to facilitate viewing and manipulation of the determined one or more related images at the client device, wherein the requested image is a medical image.

18. An apparatus according to claim 17, wherein the processor is configured to process the source image by processing the source image at a data server.

19. An apparatus according to claim 17, wherein the processor is further configured to determine a display resolution associated with the client device; and wherein the processor is configured to process the source image by processing the source image to generate a second image having a greater resolution than the source image based at least in part upon the determined display resolution.

20. An apparatus according to claim 17, wherein the processor is further configured to:

receive an indication from the client device of user manipulation of a property of the second image beyond a threshold value;

process the source image to generate a third image having a greater resolution than the second image; and provide the third image to the client device to facilitate viewing and manipulation of the third image at the client device.

21. An apparatus according to claim 17, wherein the requested image is a member of a series of images; and wherein the processor is further configured to:

retrieve additional images in the series of images from memory; and provide the additional images in the series of images to the client device to facilitate viewing and manipulation of the series of images at the client device.

22. An apparatus according to claim 17, wherein the source image is a medical image formatted in accordance with the Digital Imaging and Communications in Medicine standard data format; and wherein the processor is configured to process the source image by processing the source image to generate a second image having a greater resolution than the source image, wherein the second image is formatted such that it is viewable in a general purpose viewing agent.

* * * * *